US008697363B2

(12) United States Patent
Mir et al.

(10) Patent No.: US 8,697,363 B2
(45) Date of Patent: Apr. 15, 2014

(54) METHODS FOR DETECTING MULTIPLE TARGET NUCLEIC ACIDS IN MULTIPLE SAMPLES BY USE NUCLEOTIDE TAGS

(75) Inventors: Alain Mir, Cupertino, CA (US); Ramesh Ramakrishnan, San Jose, CA (US); Marc Unger, San Mateo, CA (US); Bernhard G. Zimmermann, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 621 days.

(21) Appl. No.: 12/548,132

(22) Filed: Aug. 26, 2009

(65) Prior Publication Data

US 2010/0120038 A1  May 13, 2010

Related U.S. Application Data

(60) Provisional application No. 61/092,010, filed on Aug. 26, 2008, provisional application No. 61/098,621, filed on Sep. 19, 2008, provisional application No. 61/146,567, filed on Jan. 22, 2009.

(51) Int. Cl.
  *C12Q 1/68* (2006.01)
(52) U.S. Cl.
  USPC ........................................................ 435/6.12
(58) Field of Classification Search
  None
  See application file for complete search history.

(56) References Cited

U.S. PATENT DOCUMENTS

| | | | |
|---|---|---|---|
| 4,683,202 A | 7/1987 | Mullis | |
| 5,066,584 A | 11/1991 | Gyllensten et al. | |
| 6,605,451 B1 | 8/2003 | Marmaro et al. | |
| 6,824,981 B2 * | 11/2004 | Chait et al. | 435/6.11 |
| 7,153,658 B2 | 12/2006 | Andersen et al. | |
| 7,312,034 B2 * | 12/2007 | Virgos et al. | 435/6.16 |
| 8,318,434 B2 | 11/2012 | Cuppens | |
| 2003/0119004 A1 | 6/2003 | Wenz et al. | |
| 2004/0081993 A1 | 4/2004 | Cantor et al. | |
| 2004/0086892 A1 | 5/2004 | Crothers et al. | |
| 2004/0091879 A1 | 5/2004 | Nolan et al. | |
| 2004/0110191 A1 | 6/2004 | Winkler et al. | |
| 2004/0209299 A1 | 10/2004 | Pinter et al. | |
| 2004/0229349 A1 | 11/2004 | Daridon | |
| 2005/0064488 A1 | 3/2005 | Huh et al. | |
| 2005/0095634 A1 * | 5/2005 | Baker et al. | 435/6 |
| 2005/0252773 A1 | 11/2005 | McBride et al. | |
| 2005/0260640 A1 | 11/2005 | Andersen et al. | |
| 2006/0053503 A1 | 3/2006 | Culiat et al. | |
| 2007/0020640 A1 | 1/2007 | McCloskey et al. | |
| 2007/0219364 A1 | 9/2007 | Andersen et al. | |
| 2008/0108063 A1 | 5/2008 | Lucero et al. | |
| 2008/0223721 A1 | 9/2008 | Cohen et al. | |
| 2009/0053719 A1 | 2/2009 | Lo et al. | |
| 2009/0163366 A1 | 6/2009 | Nickerson et al. | |
| 2009/0239308 A1 | 9/2009 | Dube et al. | |
| 2009/0317798 A1 | 12/2009 | Heid et al. | |
| 2010/0178655 A1 | 7/2010 | Hamilton et al. | |
| 2010/0203538 A1 | 8/2010 | Dube et al. | |
| 2010/0273219 A1 | 10/2010 | May et al. | |
| 2010/0285537 A1 * | 11/2010 | Zimmermann | 435/91.2 |
| 2011/0053806 A1 | 3/2011 | Amin | |
| 2011/0129841 A1 | 6/2011 | Heid et al. | |
| 2011/0143949 A1 | 6/2011 | Heid et al. | |
| 2013/0005585 A1 | 1/2013 | Anderson et al. | |

FOREIGN PATENT DOCUMENTS

| | | |
|---|---|---|
| CN | 101067156 A | 11/2007 |
| EP | 0197196 A1 | 10/1986 |
| EP | 2201143 B1 | 11/2012 |
| WO | WO/01/59161 | 8/2001 |
| WO | WO/2004/051218 | 6/2004 |
| WO | WO/2005/064020 | 7/2005 |
| WO | WO/2005/107938 | 11/2005 |
| WO | WO/2006/023919 | 3/2006 |
| WO | WO/2006/128010 | 11/2006 |
| WO | WO/2007/024798 | 3/2007 |
| WO | WO/2007/044091 | 4/2007 |
| WO | WO/2010/027870 | 3/2010 |
| WO | WO/2010/115154 | 10/2010 |
| WO | WO/2012/162267 | 11/2012 |

OTHER PUBLICATIONS

Makrigiorgos et al. (A PCR-based amplification method retaining the quantitative difference between two complex genomes, Nature Biotechnology, Published online: Aug. 5, 2002, doi:10.1038/nbt724).*
U.S. Appl. No. 61/605,016, filed Feb. 29, 2012, Fowler et al.
International Search Report and Written Opinion dated Dec. 7, 2012 issued in PCT/US2012/038894 (WO/2012/162267).
US Final Office Action dated Mar. 25, 2013 issued in U.S. Appl. No. 12/753,703.
US Office Action dated Jul. 10, 2013 issued in U.S. Appl. No. 12/753,703.
CN Office Action dated Nov. 1, 2012 issued in CN200980142505.9.
CN Office Action dated Mar. 4, 2013 issued in CN201080021508.X.
EP Office Action dated Mar. 15, 2013 issued in EP10759511.8.

(Continued)

*Primary Examiner* — Christopher M Babic
*Assistant Examiner* — Aaron Priest
(74) *Attorney, Agent, or Firm* — Emily M. Haliday; Weaver Austin Villeneuve & Sampson LLP

(57) ABSTRACT

The present invention provides assay methods that increase the number of samples and/or target nucleic acids that can be analyzed in a single assay. In certain embodiments, an assay method entails separately subjecting S samples to an encoding reaction that produces a set of T tagged target nucleotide sequences, each tagged target nucleotide sequence including a sample-specific nucleotide tag and a target nucleotide sequence. In some embodiments, an assay method entails separately subjecting S samples to an encoding reaction that produces a set of T tagged target nucleotide sequences, each tagged target nucleotide sequence including a first nucleotide tag linked to a target nucleotide sequence, which is linked to a second nucleotide tag. In either case, the tagged target nucleotide sequences from the S samples can be mixed to form an assay mixture and subsequently assayed.

36 Claims, 9 Drawing Sheets

(56) References Cited

OTHER PUBLICATIONS

Guo et al. (2003) "Methodology for using a universal primer to label amplified DNA segments for molecular analysis" *Biotechnology Letters* 25:2079-2083.

Sawasaki et al. (2002) "A cell-free protein synthesis system for high-throughput proteomics" *PNAS* 99(23):14652-14657.

International Search Report and Written Opinion dated May 10, 2010 issued in PCT/US2009/055083 (WO/2010/027870).

International Preliminary Examination Report dated Mar. 10, 2011 issued in PCT/U52009/055083 (WO/2010/027870).

International Search Report and Written Opinion dated Aug. 30, 2010 issued in PCT/US2010/029854 (WO/2010/115154).

International Preliminary Examination Report dated Oct. 13, 2011 issued in PCT/US2010/029854 (WO/2010/115154).

US Office Action dated Jun. 28, 2012 issued in U.S. Appl. No. 12/753,703.

EP Extended Search Report dated Oct. 15, 2012 issued in EP09812052.0.

EP Extended Search Report dated Jul. 19, 2012 issued in EP10759511.8.

Binladen et al. (2007) "The use of coded PCR Primers enables High-Throughput Sequencing of multiple homolog amplification products by 454 parallel sequencing" *PLOS One* 2(e197): 1-9.

Brownie et al. (1997) "The elimination of primer-dimer accumulation in PCR" *Nucleic Acids Research* 25(16): 3235-3241.

Hayden et al. (2008) "Multiplex-Ready PCR: A new method for multiplexed SSR and SNP genotyping" *BMC Genomics* 9(1): 80(1-12).

Kita-Matsuo et al. (2005) "Adaptor-tagged competitive polymerase chain reaction: amplification bias and quantified gene expression levels" *Analytical Biochemistry* 339(1): 15-28.

Neilan et al. (1997) "A universal procedure for primer labeling of amplicons" *Nucleic Acids Research* 25(14): 2938-2939.

Sellner et al. (2004) "MLPA and MAPH: New Techniques for Detection of Gene Deletion" *Human Mutation* 23(5): 413-419.

Stürzenbaum (1999) "Transfer RNA Reduces the Formation of Primer Artifacts During Quantitative PCR" *BioTechniques* 27:50-52.

Teo et al. (2002) "Reliable and reproducible LightCycler qPCR for HIV-1 DNA 2-LTR circles" *Journal of Immunological Methods* 270: 109-118.

Uematsu et al. (2001) "Multiplex polymerase chain reaction (PCR) with color-tagged module-shuffling primers for comparing gene expression levels in various cells" *Nucleic Acids Research, Oxford University Press*, GB 29(16): E84(1-6).

\* cited by examiner

Truth (not Tagged)

| Assay | % Call Rate | SD |
|---|---|---|
| | % Call Rate, n=3 | |
| SNP01 | 96.4 | 1.3 |
| SNP02 | 97.8 | 0.0 |
| SNP03 | 97.8 | 0.0 |
| SNP04 | 97.1 | 1.3 |
| SNP05 | 97.1 | 1.3 |
| SNP06 | 97.8 | 0.0 |
| SNP07 | 97.8 | 0.0 |
| SNP08 | 97.8 | 0.0 |
| SNP09 | 97.8 | 0.0 |
| SNP10 | 98.6 | 1.3 |
| SNP11 | 97.1 | 1.3 |
| SNP12 | 97.8 | 0.0 |
| SNP13 | 95.7 | 0.0 |
| SNP14 | 95.7 | 0.0 |
| SNP15 | 97.8 | 0.0 |
| SNP16 | 97.8 | 0.0 |
| Average | 97.4 | 0.4 |

Std Genotyping (no tagging)
Invalids, no calls removed
Mean Call rate = 97.4%

Test (Tagged)

| Assay | % Call Rate by Tag | | |
|---|---|---|---|
| | 1 | 2 | 3 |
| SNP01 | 100 | 100 | 97.9 |
| SNP02 | 100 | 100 | 97.9 |
| SNP03 | 100 | 100 | 97.9 |
| SNP04 | 100 | 100 | 97.9 |
| SNP05 | 100 | 100 | 97.9 |
| SNP06 | 100 | 100 | 100 |
| SNP07 | 100 | 100 | 100 |
| SNP08 | 100 | 100 | 98 |
| SNP09 | 100 | 100 | 100 |
| SNP10 | 100 | 100 | 97.9 |
| SNP11 | 100 | 100 | 97.9 |
| SNP12 | 100 | 100 | 97.9 |
| SNP13 | 100 | 100 | 97.9 |
| SNP14 | 100 | 100 | 100 |
| SNP15 | 100 | 100 | 100 |
| SNP16 | 100 | 100 | 100 |
| Average | 100 | 100 | 98.8 |

Tagged Genotyping
Same DNA, Same assays
Mean call rate 98.8 - 100%

*Figure 3*

METHODS FOR DETECTING MULTIPLE TARGET NUCLEIC ACIDS IN MULTIPLE SAMPLES BY USE NUCLEOTIDE TAGS

CROSS-REFERENCE TO RELATED APPLICATIONS

This application claims the benefit of U.S. provisional application Nos. 61/092,010, filed Aug. 26, 2008; 61/098,621, filed Sep. 19, 2008; and 61/146,567, filed Jan. 22, 2009, which are hereby incorporated by reference in their entireties.

FIELD OF THE INVENTION

The present invention relates generally to the area of high-throughput assays for detection of particular target nucleic acids. In particular, the invention relates to methods for increasing the number of samples and/or targets that can be analyzed in a single assay.

BACKGROUND OF THE INVENTION

The ability to detect specific nucleic acid sequences in a sample has resulted in new approaches in diagnostic and predictive medicine, environmental, food and agricultural monitoring, molecular biology research, and many other fields.

Additional methods, especially methods that allow detection of many targets and/or the analysis of many samples simultaneously across a broad range of concentrations in a sample would be of great benefit.

SUMMARY OF THE INVENTION

The invention provides a first assay method for detecting a plurality of target nucleic acids (i.e., T target nucleic acids, where T is an integer greater than one) in a plurality of samples. In certain embodiments, the method entails providing S samples that will be mixed together prior to assay, where S is an integer greater than 1. Each of these samples can be separately subjected to an encoding reaction that produces a set of T tagged target nucleotide sequences, each tagged target nucleotide sequence comprising a sample-specific nucleotide tag and a target nucleotide sequence. For each of these S samples (i.e., each of the samples to be combined), the tagged target nucleotide sequences can be mixed to form an assay mixture. In this manner, samples can be assayed in batches, so that, if, e.g., 48 samples are to be analyzed, S can be, e.g., 3, which means that 16 assay mixtures are prepared. See Example 1. The assay mixture, or aliquots thereof, can be subjected to amplification using S×T unique pairs of amplification primers, wherein each amplification primer pair comprises:

a forward or a reverse amplification primer that anneals to a target nucleotide sequence; and a reverse or a forward amplification primer, respectively, that anneals to a sample-specific nucleotide tag. For each unique primer pair, the presence or, in particular embodiments, amount an amplification product is in the amplification mixture, or aliquot thereof, is determined. The presence or amount of an amplification product indicates the presence or amount of a particular target nucleic acid in a particular sample.

In illustrative embodiments of the first assay method, the encoding reaction comprises separately subjecting each of the S samples to preamplification using a distinct set of forward and reverse preamplification primers for each sample to produce preamplified samples, wherein:

each preamplification primer set comprises T pairs of forward and reverse preamplification primers, wherein each preamplification primer pair is capable of amplifying a particular target nucleic acid; and either all forward preamplification primers or all reverse preamplification primers in a given set comprise a common sample-specific nucleotide tag.

The preamplified samples for each of the S samples are mixed to form an assay mixture (e.g., one assay mixture for each set of samples to be analyzed together). The assay mixture can then be analyzed by dividing it into up to S×T amplification mixtures, and separately subjecting each of the amplification mixtures to amplification using a unique pair of amplification primers, wherein each amplification primer pair comprises:

a forward or a reverse amplification primer that anneals to a target nucleotide sequence; and a reverse or a forward amplification primer, respectively, that anneals to a sample-specific nucleotide tag.

The presence or amount of an amplification product in the amplification mixtures is determined to determine the presence or amount of a particular target nucleic acid in a particular sample.

The invention provides a second assay method for detecting a plurality of target nucleic acids (i.e., T target nucleic acids, where T is an integer greater than one) in a plurality of samples. In certain embodiments, the method entails providing S samples that will be mixed together prior to assay, where S is an integer greater than 1. Each of these samples is separately subjected to an encoding reaction that produces a set of T tagged target nucleotide sequences, each tagged target nucleotide sequence comprising a first nucleotide tag linked to a target nucleotide sequence, which is linked to a second nucleotide tag. For each of these S samples (i.e., each of the samples to be combined), the tagged target nucleotide sequences are mixed to form an assay mixture. The assay mixture, or aliquots thereof, is subjected to amplification using S×T unique pairs of amplification primers, wherein each amplification primer pair comprises:

a forward or a reverse amplification primer that anneals to a first nucleotide tag; and a reverse or a forward amplification primer, respectively, that anneals to a second nucleotide tag.

For each unique primer pair, the presence or amount of an amplification product in the amplification mixture, or aliquot thereof, is determined. The presence of an amplification product indicates the presence or amount of a particular target nucleic acid in a particular sample.

In exemplary embodiments of the second assay method, the encoding reaction comprises separately subjecting each of the S samples to preamplification using a distinct set of forward and reverse preamplification primers for each sample to produce preamplified samples, wherein:

each preamplification primer set comprises T pairs of forward and reverse preamplification primers, wherein each preamplification primer pair is capable of amplifying a particular target nucleic acid; and each forward preamplification primer comprises a forward nucleotide tag, and each reverse preamplification primer comprises a reverse nucleotide tag;

The preamplified samples for each of the S samples are mixed to form an assay mixture. The assay mixture can then be analyzed by dividing each assay mixture into up to S×T amplification mixtures, and separately subjecting each of the amplification mixtures to amplification using a unique pair of amplification primers, wherein each amplification primer pair comprises:

a forward amplification primer that anneals to a forward nucleotide tag; and a reverse amplification primer that anneals to a reverse nucleotide tag.

The presence or amount of an amplification product present in the amplification mixtures is determined. The presence of an amplification product indicates the presence or amount of a particular target nucleic acid in a particular sample.

The invention also provides a third assay method, which detects a plurality of target nucleic acids (i.e., T target nucleic acids) in a sample. The method entails providing T forward preamplification primers to a sample, wherein each forward preamplification primer comprises a different target-specific nucleotide sequence and a set-specific nucleotide tag, wherein X different forward set-specific nucleotide tags are employed, and X is an integer that is greater than 1 and less than T, whereby T/X primers comprise the same forward set-specific nucleotide tag. Also provided to the sample are T reverse preamplification primers, wherein each reverse preamplification primer comprises a different target-specific nucleotide sequence and a reverse set-specific nucleotide tag, wherein Y different reverse set-specific nucleotide tags are employed, and Y is an integer that is greater than 1 and less than T, whereby T/Y primers comprise the same reverse set-specific nucleotide tag. The sample is subjected to preamplification to produce an assay mixture, wherein any preamplification product produced for a particular target incorporates a unique combination of forward and reverse set-specific nucleotide tags. The assay mixture, or aliquots thereof, to amplification using amplification primers wherein each amplification primer pair comprises:

a forward amplification primer that anneals to the forward set-specific nucleotide tag; and a reverse amplification primer that anneals to the reverse set-specific nucleotide tag. For each unique primer pair, the presence or amount of an amplification product in the amplification mixture, or aliquot thereof, is determined. The presence of an amplification product indicates the presence of a particular target nucleic acid in the sample.

A fourth assay method of the invention provides a modular approach to detecting a plurality target nucleic acids in a sample. This method entails dividing a sample into R aliquots, wherein R is an integer greater than 1. Each of the R aliquots is separately subjected to an encoding reaction that produces a set of T tagged target nucleotide sequences, wherein T is the number of target nucleic acids to be detected in each aliquot, T being an integer greater than 1. Each tagged target nucleotide sequence comprises a first nucleotide tag 5' of a target nucleotide sequence, a target nucleotide sequence, and a second nucleotide tag 3' of the target nucleotide sequence. The combination of nucleotide tags in each of said T tagged target nucleotide sequences is unique for every tagged target nucleotide sequence in each aliquot. However, the same set of first and second nucleotide tag combinations is used in the encoding reaction in each of the aliquots. This aspect of the method makes it possible to separately subject each aliquot to amplification using the same set of T different amplification primer pairs for each aliquot. Each primer pair includes a first primer that anneals to the first nucleotide tag and a second primer that anneals to the second nucleotide tag in each tagged target nucleotide sequence. For each unique primer pair in each aliquot, the method entails determining whether an amplification product is present in the aliquot. The presence of an amplification product indicates the presence of a particular target nucleic acid in the sample.

In a variation of this method, after the encoding reaction, each aliquot is divided into T sub-aliquots. One of the T different amplification primer pairs is combined with each sub-aliquot, and the sub-aliquots are subjected to separate amplification reactions.

In particular embodiments of the above-described methods, the sample can be a genomic DNA sample. In variations of these embodiments, preamplification of genomic DNA can be conducted in the presence of an amount of a blocking agent that is sufficient to increase specific amplification of the target nucleic acid.

BRIEF DESCRIPTION OF THE DRAWINGS

The invention may be understood by reference to the following description taken in conjunction with the accompanying drawings that illustrate certain specific embodiments of the present invention.

FIG. 3 shows the data from the genotyping study of Example 2. 16 SNP loci were genotyped using tagging and, for comparison, standard methodologies. Untagged samples are described as "Truth." The same untagged samples shown in the "Truth" table were compared against samples bearing Tag sequences 1, 2, or 3 on the forward primer ("Test") as described in Example 2. Tagged samples display 1.4-to-2% increase in call rate. All no-called SNPs in Tag 3 were derived from a single sample.

DETAILED DESCRIPTION

Figure 1:
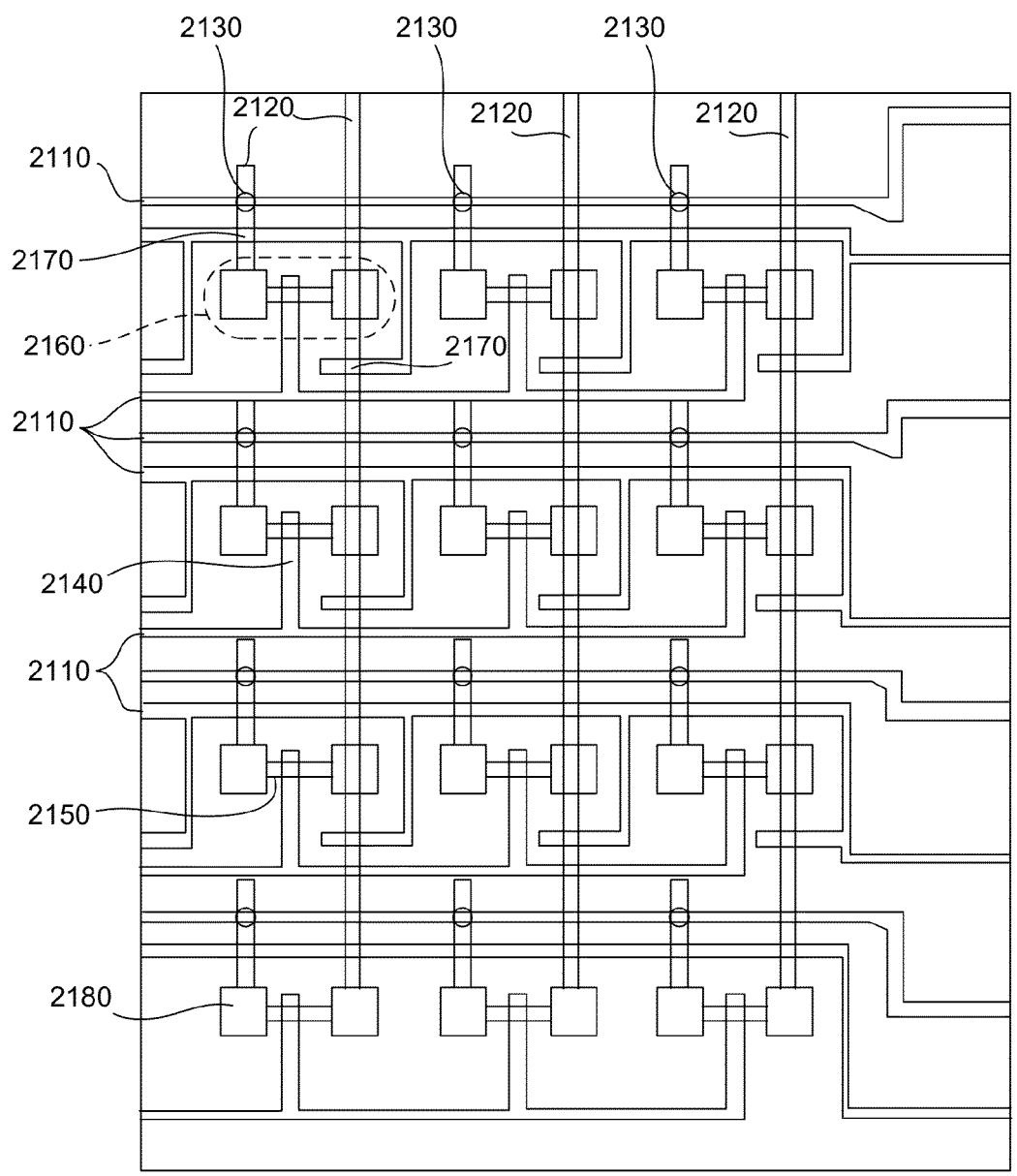
FIG. 1 depicts an exemplary matrix-type microfluidic device plan view.

The present invention provides methods for increasing the number of samples that can be analyzed for one or multiple targets in a single assay, as well as methods for increasing the number of targets that can be analyzed in a sample, while minimizing increases in assay cost. The methods are particularly well-suited for increasing the efficiency of assays performed on matrix-type microfluidic devices.

It is understood that the invention is not limited to the particular methodology, protocols, and reagents, etc., described herein, as these can be varied by the skilled artisan. It is also understood that the terminology used herein is used for the purpose of describing particular illustrative embodiments only, and is not intended to limit the scope of the invention. It also noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention.

DEFINITIONS

Terms used in the claims and specification are defined as set forth below unless otherwise specified. These terms are defined specifically for clarity, but all of the definitions are consistent with how a skilled artisan would understand these terms.

The term "adjacent," when used herein to refer two nucleotide sequences in a nucleic acid, can refer to nucleotide sequences separated by 0 to about 20 nucleotides, more specifically, in a range of about 1 to about 10 nucleotides, or sequences that directly abut one another. In addition, two primers may be said to be adjacent if they overlap, for example adjacent primers can overlap by about 1 to about 4 nucleotides.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acid, as well as single-stranded molecules. In double- or triple-stranded nucleic acids, the nucleic acid strands need not be coextensive (i.e, a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The term "target nucleic acids" is used herein to refer to particular nucleic acids to be detected in the methods of the invention.

As used herein the term "target nucleotide sequence" refers to a molecule that includes the nucleotide sequence of a target nucleic acid, such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41(\% \text{ G+C})$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Exemplary stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence. For example, in certain embodiments, amplification primers used herein are said to "anneal to a sample-specific nucleotide tag." This description encompasses primers that anneal wholly to the nucleotide tag, as well as primers that anneal partially to the nucleotide tag and partially to an adjacent nucleotide sequence, e.g., a target nucleotide sequence. Such hybrid primers can increase the specificity of the amplification reaction.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

A primer pair is said to be "unique" if it can be employed to specifically amplify a particular target nucleotide sequence in a given amplification mixture.

A second primer pair is "nested" relative to a first primer pair if the first primer pair is employed to amplify a first amplification product and then the second primer pair is employed to amplify a target nucleotide sequence within the first amplification product. Nesting can be used increase the specificity of the amplification reaction.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-20 nucleotides in length).

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

The term "nucleotide tag" is used herein to refer to a predetermined nucleotide sequence that is added to a target nucleotide sequence. The nucleotide tag can encode an item of information about the target nucleotide sequence, such the identity of the target nucleotide sequence, the chromosome from which that sequence derives, or the identity of the sample from which the target nucleotide sequence was derived. In certain embodiments, such information may be encoded in one or more nucleotide tags, e.g., a combination of two nucleotide tags, one on either end of a target nucleotide sequence, can encode the identity of the target nucleotide sequence.

As used herein, the term "encoding reaction" refers to reaction in which at least one nucleotide tag is added to a target nucleotide sequence. Nucleotide tags can be added, for example, by an "encoding PCR" in which the at least one primer comprises a target-specific portion and a nucleotide tag located on the 5' end of the target-specific portion, and a second primer that comprises only a target-specific portion or a target-specific portion and a nucleotide tag located on the 5' end of the target-specific portion. For illustrative examples of PCR protocols applicable to encoding PCR, see pending WO Application US03/37808 as well as U.S. Pat. No. 6,605,451. Nucleotide tags can also be added by an "encoding ligation" reaction that can comprise a ligation reaction in which at least one primer comprises a target-specific portion and nucleotide tag located on the 5' end of the target-specific portion, and a second primer that comprises a target-specific portion only or a target-specific portion and a nucleotide tag located on the 5' end of the target specific portion. Illustrative encoding ligation reactions are described, for example, in U.S. Patent Publication No. 2005/0260640, which is hereby incorporated by reference in its entirety, and in particular for ligation reactions. An encoding reaction, such as encoding PCR, can be carried out in 1 cycle, which is sufficient to add a single nucleotide tag. Alternatively, an encoding reaction, such as encoding PCR, can be carried out for multiple cycles to preamplify target nucleic acids (e.g., to increase concentration).

As used herein an "encoding reaction" produces a "tagged target nucleotide sequence," which includes a nucleotide tag linked to a target nucleotide sequence.

The term "sample-specific" nucleotide tag is used herein to refer to a nucleotide tag that encodes the identity of the sample of the target nucleotide sequence to which the tag is, or becomes, linked in an encoding reaction.

As used herein with reference to a portion of a primer, the term "target-specific nucleotide sequence" refers to a sequence that can specifically anneal to a target nucleic acid or a target nucleotide sequence under suitable annealing conditions.

A "common" sample-specific nucleotide tag refers to a tag having a specific nucleotide sequence that is, or becomes, linked to all target nucleotide sequences produced during an encoding reaction, such that all tagged target nucleotide sequences produced from a given sample are each identified by a tag having the same sequence.

A "set-specific nucleotide tag" is a tag that is, or becomes, linked to a plurality of target nucleotide sequences. In certain embodiments of the invention, an assay mixture can comprise multiple tagged target nucleotide sequence sequences having different set-specific nucleotide tags at either end that, in combination, uniquely identify each tagged target nucleotide sequence.

The phrase "a distinct set of forward and reverse primers" refers to a set of primers that is distinguishable from any other sets of primers employed in an assay. Such a set of primers can be used to introduce sample-specific nucleotide tags.

Amplification according to the present teachings encompasses any means by which at least a part of at least one target nucleic acid is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—

CCR), digital amplification, and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol. Diagn. 2002 November; 2(6): 542-8., Cook et al., J Microbiol Methods. 2003 May; 53(2):165-74, Schweitzer et al., Curr Opin Biotechnol. 2001 February; 12(1):21-7, U.S. Pat. No. 5,830,711, U.S. Pat. No. 6,027,889, U.S. Pat. No. 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

The term "qPCR" is used herein to refer to quantitative real-time polymerase chain reaction (PCR), which is also known as "real-time PCR" or "kinetic polymerase chain reaction."

The term "digital amplification" is used herein to refer to an amplification method in which identical (or substantially similar) amplification reactions are run on a nucleic acid sample, such as genomic DNA. Generally, the quantity of nucleic acid subjected to digital amplification is generally selected such that, when distributed into discrete reaction mixtures, each individual amplification reaction is expected to include one or fewer amplifiable nucleic acids. The concentration of any target amplicon (copies/µL) is correlated with the number of positive (i.e., amplification product-containing) reaction mixtures. See copending U.S. application Ser. No. 12/170,414, entitled "Method and Apparatus for Determining Copy Number Variation Using Digital PCR," which is incorporated by reference for all purposes, and, in particular, for analysis of digital PCR results. Also see Dube et al., 2008, "Mathematical Analysis of Copy Number Variation in a DNA Sample Using Digital PCR on a Nanofluidic Device" PLoS ONE 3(8): e2876. Where PCR is used for amplification, digital amplification is termed "digital PCR."

A "reagent" refers broadly to any agent used in a reaction, other than the analyte (e.g., nucleic acid being analyzed). Exemplary reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators.

The term "universal detection probe" is used herein to refer to any probe that identifies the presence of an amplification product, regardless of the identity of the target nucleotide sequence present in the product.

The term "universal qPCR probe" is used herein to refer to any such probe that identifies the presence of an amplification product during qPCR. In particular embodiments, nucleotide tags according to the invention can comprise a nucleotide sequence to which a detection probe, such as a universal qPCR probe binds. Where a tag is added to both ends of a target nucleotide sequence, each tag can, if desired, include a sequence recognized by a detection probe. The combination of such sequences can encode information about the identity, chromosomal origin, or sample source of the tagged target nucleotide sequence. In other embodiments, one or more amplification primers can comprise a nucleotide sequence to which a detection probe, such as a universal qPCR probe binds. In this manner, one, two, or more probe binding sites can be added to an amplification product during the amplification step of the methods of the invention. Those of skill in the art recognize that the possibility of introducing multiple probe binding sites during preamplification (if carried out) and amplification facilitates multiplex detection, wherein two or more different amplification products can be detected in a given amplification mixture or aliquot thereof.

The term "universal detection probe" is also intended to encompass primers labeled with a detectable label (e.g., a fluorescent label), as well as non-sequence-specific probes, such as DNA binding dyes, including double-stranded DNA (dsDNA) dyes, such as SYBR Green.

The term "target-specific qPCR probe" is used herein to refer to a qPCR probe that identifies the presence of an amplification product during qPCR, based on hybridization of the qPCR probe to a target nucleotide sequence present in the product.

"Hydrolysis probes" are generally described in U.S. Pat. No. 5,210,015, which is incorporated herein by reference in its entirety for its description of hydrolysis probes. Hydrolysis probes take advantage of the 5'-nuclease activity present in the thermostable Taq polymerase enzyme typically used in the PCR reaction (TAQMAN® probe technology, Applied Biosystems, Foster City Calif.). The hydrolysis probe is labeled with a fluorescent detector dye such as fluorescin, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe anneals downstream of one of the primers that defines one end of the target nucleic acid in a PCR reaction. Using the polymerase activity of the Taq enzyme, amplification of the target nucleic acid is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe. The hydrolysis reaction irrevocably releases the quenching effect of the quencher dye on the reporter dye, thus resulting in increasing detector fluorescence with each successive PCR cycle. In particular, hydrolysis probes suitable for use in the invention can be capable of detecting 8-mer or 9-mer motifs that are common in the human and other genomes and/or transcriptomes and can have a high $T_m$ of about 70° C. enabled by the use of linked nucleic acid (LNA) analogs.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," as used herein, generally refers to any organic or inorganic molecule that absorbs electromagnetic radiation at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

A "polymorphic marker" or "polymorphic site" is a locus at which nucleotide sequence divergence occurs. Exemplary markers have at least two alleles, each occurring at frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

Detection of Multiple Target Nucleic Acids in Multiple Samples

In General

In various embodiments, methods are provided for detecting a plurality of target nucleic acids (i.e., T target nucleic acids, where T is an integer greater than one) in a plurality of samples. In certain embodiments, the method entails providing S samples that will be mixed together (i.e., pooled) prior to assay, where S is an integer greater than 1. Each of these samples is separately subjected to an encoding reaction that produces a set of T tagged target nucleotide sequences, wherein each nucleotide tag encodes information about the identity and/or sample source of a particular target nucleic acid. For each of these S samples (i.e., each of the samples to be pooled), the tagged target nucleotide sequences are mixed to form an assay mixture. In this manner, samples can be assayed in batches, so that, if, e.g., 48 samples are to be analyzed, S can be, e.g., 3, which means that 16 assay mixtures can be prepared to detect 16 different targets. The first assay mixture can contain, e.g., tagged target nucleotide sequences from samples 1-3, the second assay mixture can contain, e.g., tagged target nucleotide sequences from samples 4-6, and so on. See Example 1. An amplification step is then carried out, whereby the tagged target nucleotide sequences are amplified using at least one primer that anneals to at least one nucleotide tag.

If greater specificity is desired, one or both amplification primers can include one or more nucleotides that are complementary to the target nucleotide(s) adjacent to the nucleotide tag(s), i.e., hybrid amplification primers including target-specific sequences, as well as tag-specific sequences can be employed. In certain embodiments, the target-specific sequences are 3' of the tag-specific sequences in the primer.

In principle, the methods described herein are applicable to the detection of as many targets in as many samples as desired. However, the assay format will often dictate the total number of detections that can be performed conveniently without multiplexing, for example, by using more than one type of label. As discussed in detail below, assay mixtures can be aliquoted for separate amplification in, for example, a microtiter plate, or, more typically, a matrix-type microfluidic device. In particular embodiments, S (number of samples that are mixed)×T (number of targets) defines the number of assay mixture aliquots, which can be, e.g., 30, 48, 96, 120, or 192 for analysis on a matrix-type microfluidic device having the corresponding number of isolated reaction chambers. In exemplary embodiments, the product of the total number of samples assayed in a single assay×T is at least a value selected from the group consisting of 2304, 3600, 4608, and 9216. As those of skill in the art appreciate, additional increases in throughput can be achieved by multiplexing, for example, by using multiple labels to perform multiple detections in a given assay aliquot.

Target Nucleotide Sequences Tagged with One Sample-Specific Nucleotide Tag

In particular embodiments, each tagged target nucleotide sequence includes a sample-specific nucleotide tag and a target nucleotide sequence. In such embodiments, the assay mixture, or aliquots thereof, is subjected to amplification using S×T unique pairs of amplification primers, wherein each amplification primer pair includes:

a forward or a reverse amplification primer that anneals to a target nucleotide sequence; and a reverse or a forward amplification primer, respectively, that anneals to a sample-specific nucleotide tag. Amplification is therefore dependent upon the presence of a tagged target nucleotide sequence that has a particular target nucleotide sequence and a particular sample-specific tag. Thus, the production of an amplification product including these nucleotide sequences indicates the presence and, if quantitative detection is employed, the amount of a particular target nucleic acid in a particular sample.

The presence or amount of the amplification product of a unique primer pair can be detected using any means capable of detecting the presence of a target nucleotide sequence in combination with a particular sample-specific tag. For ease of detection, an assay mixture can be analyzed by dividing it into up to S×T amplification mixtures, and separately subjecting each of the amplification mixtures to amplification using a unique pair of amplification primers. In this case, the presence or amount of an amplification product in a particular aliquot indicates the presence or amount of the target nucleic acid corresponding to the target-specific primer in the sample corresponding to the sample-specific nucleotide tag.

The nucleotide sequence of the sample-specific nucleotide tag encodes sample identity. All tagged target nucleotide sequences produced from a given sample can be tagged with a common sample-specific nucleotide tag, i.e., one that has the same nucleotide sequence. Alternatively, every target nucleotide sequence in an assay mixture can be tagged with a distinct sample-specific nucleotide tag, i.e., such that each tagged target nucleotide sequence in the assay mixture bears a sample-specific nucleotide tag having a different nucleotide sequence. Thus, if there are three samples that will be pooled for analysis of 16 targets in one assay mixture, tags 1-16 could be employed to identify target nucleic acid sequences from sample 1, tags 17-32 could be employed to identify target nucleic acid sequences from sample 2, and tags 32-48 could be employed to identify target nucleic acid sequences from sample 3. As those of skill in the art appreciate, sets of tags could be employed such that some, but not all, target nucleotide sequences from a given sample share a common tag. Thus, for example, tag 1 could be employed to identify target nucleic acid sequences 1-4 from sample 1, tag 2 could be employed to identify target nucleic acid sequences 5-8 from sample 1, tag 3 could be employed to identify target nucleic acid sequences 9-12 from sample 1, and tag 4 could be employed to identify target nucleic acid sequences 13-16 from sample. In this instance, tags 1-4 would identify sample 1 target nucleic acid sequences, and similar sets of tags (e.g., tags 5-8 and tags 9-12) would identify sample 2 and 3 target nucleic acid sequences.

In exemplary embodiments of this method, the encoding reaction entails separately subjecting each of the S samples to preamplification using a distinct set of forward and reverse preamplification primers for each sample to produce preamplified samples, wherein each preamplification primer set comprises T pairs of forward and reverse preamplification primers, wherein each preamplification primer pair is capable of amplifying a particular target nucleic acid. In addition, all forward preamplification primers or all reverse preamplification primers in a given set comprise a sample-specific nucleotide tag, which can, but need not, be a common sample-specific nucleotide tag. The sample-specific nucleotide tag is generally 5' of the target-specific nucleotide sequence in the primer.

The preamplified samples for each of the S samples are mixed to form an assay mixture (e.g., one assay mixture for each set of samples to be analyzed together). The assay mixture can then be analyzed as described above. Each forward preamplification primer in a set can include a sample-specific nucleotide tag, in addition to a target-specific nucleotide sequence, and each reverse preamplification primer in the set can include a target-specific nucleotide sequence. Alternatively, each forward preamplification primer in a set can include a target-specific nucleotide sequence, and each reverse preamplification primer in each set can include a sample-specific nucleotide tag, in addition to a target-specific nucleotide sequence.

Target Nucleotide Sequences Tagged with Two Nucleotide Tags

In particular embodiments, each tagged target nucleotide sequence includes a a first nucleotide tag linked to a target nucleotide sequence, which is linked to a second nucleotide tag. In such embodiments, the assay mixture, or aliquots thereof, is subjected to amplification using S×T unique pairs of amplification primers, wherein each amplification primer pair includes:

a forward or a reverse amplification primer that anneals to a first nucleotide tag; and a reverse or a forward amplification primer, respectively, that anneals to a second nucleotide tag. Amplification is therefore dependent upon the presence of a tagged target nucleotide sequence that has the proper combination of tags.

The nucleotide sequence of the nucleotide tag can encode sample identity in the various ways described above for embodiments employing a single sample-specific tag. In other words, all tagged target nucleotide sequences produced from a given sample can be tagged with a common sample-specific nucleotide tag. Alternatively, every target nucleotide sequence in an assay mixture can be tagged with a distinct sample-specific nucleotide tag, or sets of tags could be employed such that some, but not all, target nucleotide sequences from a given sample share a common tag. Because two tags are used, any of these strategies can be employed in combination. For example, one tag can be a sample-specific tag common to all tagged target nucleotide sequences produced from a given sample, whereas the other tag can be distinct for every tagged nucleotide sequence in an assay mixture. In certain high-specificity embodiments, every tag in an assay mixture is distinct (different in nucleotide sequence) from every other tag in the mixture.

In exemplary embodiments of this dual tagging method, the encoding reaction entails separately subjecting each of said S samples to preamplification using a distinct set of forward and reverse preamplification primers for each sample to produce preamplified samples, wherein each preamplification primer set comprises T pairs of forward and reverse preamplification primers (i.e., one for each target), wherein each preamplification primer pair is capable of amplifying a particular target nucleic acid. Additionally, each forward preamplification primer comprises a forward nucleotide tag, and each reverse preamplification primer comprises a reverse nucleotide tag. These tags are generally 5' of the target-specific nucleotide sequence in the primer.

The preamplified samples for each of the S samples are mixed to form an assay mixture (e.g., one assay mixture for each set of samples to be analyzed together). The assay mixture can then be analyzed by amplification as described generally above. Each amplification primer pair includes:

a forward amplification primer that anneals to a forward nucleotide tag; and a reverse amplification primer that anneals to a reverse nucleotide tag.

Detection of Multiple Target Nucleic Acids Through Combinatorial Tagging

The invention also provides a dual tagging assay method that is useful for detecting a plurality of target nucleic acids in a sample. This method entails providing T forward preamplification primers to a sample, wherein T is the number of targets to be detected. Each forward preamplification primer includes a different target-specific nucleotide sequence and a set-specific nucleotide tag. The set-specific nucleotide tag is generally 5' of the target-specific nucleotide tag. X different forward set-specific nucleotide tags are employed, and X is an integer that is greater than 1 and less than T. Thus, T/X primers comprise the same forward set-specific nucleotide tag.

Also provided to the sample are T reverse preamplification primers. Each reverse preamplification primer includes a different target-specific nucleotide sequence and a reverse set-specific nucleotide tag. The set-specific nucleotide tag is generally 5' of the target-specific nucleotide tag. Y different reverse set-specific nucleotide tags are employed, and Y is an integer that is greater than 1 and less than T. Thus, T/Y primers comprise the same reverse set-specific nucleotide tag.

The sample is subjected to preamplification to produce an assay mixture, wherein any preamplification product produced for a particular target incorporates a unique combination of forward and reverse set-specific nucleotide tags. An amplification step is then carried out, whereby the tagged target nucleotide sequences are amplified by the proper combination of amplification primers, namely those that anneal to the nucleotide tags present in a particular tagged nucleotide sequence.

Thus, where X+Y primers are prepared, X×Y targets can be analyzed in a single assay. For example, if X and Y are each 100, only 200 primers need be synthesized to detect 10,000 target nucleic acids.

In exemplary embodiments of this method, the amplification is carried out by dividing the assay mixture into T amplification mixtures, and separately amplifying each of said amplification mixtures using a unique pair of amplification primers. Each amplification primer pair includes:
  a forward amplification primer that anneals to the forward set-specific nucleotide tag; and
  a reverse amplification primer that anneals to the reverse set-specific nucleotide tag.
For each unique primer pair, the presence or amount of an amplification product in the amplification mixture, or aliquot thereof, is determined. The presence of an amplification product indicates the presence of a particular target nucleic acid in the sample.

In principle, the methods of the invention are applicable to the detection of as many targets in as many samples as desired. However, the assay format will often dictate the total number of detections that can be performed conveniently without multiplexing, for example, by using more than one type of label. In particular embodiments, assay mixtures are aliquoted for separate amplification in, for example, a microtiter plate, or, more typically, a matrix-type microfluidic device. Current microfluidic device designs lend themselves to assays in which X or Y is at least a value selected from 12, 24, 48, and 96, and where T (the number of targets detected) is at least a value selected from the group consisting of 384, 576, 768, 1152, 2304, 3600, 4608, and 9216. As those of skill in the art appreciate, additional increases in throughput can be achieved by multiplexing, for example, by using multiple labels to perform multiple detections in a given assay aliquot.

The invention also contemplates combinations of the tagging methods described above.

Detection of Multiple Target Nucleic Acids—Modular Approach

The invention also provides an assay method for detecting a plurality of target nucleic acids in a sample, wherein the target nucleic acids to be detected are divided into sets or "modules," each module of target nucleic acids is tagged with the same set of nucleotide tag pairs. Within each module, the sets of tag pairs differ from one another, but same set of tag pairs is used for each module. Detection can then be carried out by amplifying each module with a set of primer pairs that anneals to the set of tag pairs.

More specifically, in certain embodiments, the method entail dividing a sample into R aliquots, wherein R is an integer greater than 1 (e.g., 96). Each of the R aliquots can be separately subjected to an encoding reaction that produces a set of T tagged target nucleotide sequences, wherein T is the number of target nucleic acids to be detected in each aliquot, T being an integer greater than one (e.g., 96). Each tagged target nucleotide sequence includes a first nucleotide tag 5' of a target nucleotide sequence, a target nucleotide sequence, and a second nucleotide tag 3' of the target nucleotide sequence. The combination of nucleotide tags in each of said T tagged target nucleotide sequences is unique for every tagged target nucleotide sequence in each aliquot. However, the same set of first and second nucleotide tag combinations is used in the encoding reaction in each of the aliquots. Thus, in certain embodiments, the combination of nucleotide tags in each of said T tagged target nucleotide sequences is present in a tagged target nucleotide sequence in each of the other aliquots, although each tag combination can be attached to a different target nucleotide sequence. Accordingly, in particular embodiments the encoding reaction can produce up to R×T (e.g., 96×96=9216) different tagged target nucleotide sequences, thus permitting the assay of R×T (e.g., 9216).

Detection of the tagged target nucleotide sequences can be carried out by separately subjecting each aliquot to amplification using the same set of T different amplification primer pairs for each aliquot, each primer pair including a first primer that anneals to the first nucleotide tag and a second primer that anneals to the second nucleotide tag in each tagged target nucleotide sequence. The presence of an amplification product corresponding to each unique primer pair in each aliquot indicates the presence of a particular target nucleic acid in the sample.

In certain embodiments, prior to amplification, each aliquot can be divided into T sub-aliquots. Then, one of a set of T different amplification primer pairs can be combined with each sub-aliquot, and the sub-aliquots can be subjected to separate amplification reactions.

In illustrative embodiments, the encoding reaction can be a preamplification reaction, which may be carried out on a microfluidic device. To increase target nucleic acid concentration prior to encoding, an optional pre-preamplification reaction can be carried out before the encoding preamplification reaction. The pre-preamplification can be carried out in multplex. For example, target-specific primers for 9216 different target nucleic acids can be employed in one mixture. This mixture can then be divided into R=96 aliquots and each aliquot subjected to an encoding preamplification reaction on a microfluidic device, using T=96 different primer pairs that add 96 different nucleotide tag pairs to the target nucleotide sequences in each of the 96 aliquots. To increase specificity, the primers employed for preamplification can be nested relative to primers employed for pre-preamplification.

After the encoding preamplification reaction, amplification can be carried out in separate chambers of a microfluidic device. For example, each of the 96 aliquots produced upon encoding preamplification can be loaded into individual sample lines of a matrix-type microfluidic device, and each of 96 different tag-specific primer combinations can be loaded into individual assay columns. Each different of the 96 primer combination can amplify a different target nucleic acid in each of the 96 aliquots. The resulting 9216 reaction chambers (sub-aliquots) can then be subjected to amplification, followed by detection of amplification product(s), which can be carried out by any suitable means, including SYBR Green, universal probe library, use of one probe per tag combination (e.g., wherein probe sequences are introduced into nucleotide tags), use of fluorescent primers to add nucleotide tags.

In particular embodiments, this modular approach is extremely flexible and can be easily expanded by additional targets (e.g., an additional 96 targets). It is thus well-suited for assay panels.

Sample Nucleic Acids

Preparations of nucleic acids ("samples") can be obtained from biological sources and prepared using conventional methods known in the art. In particular, DNA or RNA useful in the methods described herein can be extracted and/or amplified from any source, including bacteria, protozoa, fungi, viruses, organelles, as well higher organisms such as plants or animals, particularly mammals, and more particularly humans. Suitable nucleic acids can also be obtained from environmental sources (e.g., pond water), from man-made products (e.g., food), from forensic samples, and the like. Nucleic acids can be extracted or amplified from cells, bodily fluids (e.g., blood, a blood fraction, urine, etc.), or tissue samples by any of a variety of standard techniques. Exemplary samples include samples of plasma, serum, spinal fluid, lymph fluid, peritoneal fluid, pleural fluid, oral fluid, and external sections of the skin; samples from the respiratory, intestinal genital, and urinary tracts; samples of tears, saliva, blood cells, stem cells, or tumors. For example, samples of fetal DNA can be obtained from an embryo (e.g., from one or a few embryonic or fetal cells) or from maternal blood. Samples can be obtained from live or dead organisms or from in vitro cultures. Exemplary samples can include single cells, paraffin-embedded tissue samples, and needle biopsies. Nucleic acids useful in the invention can also be derived from one or more nucleic acid libraries, including cDNA, cosmid, YAC, BAC, P1, PAC libraries, and the like.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the amplification steps of the methods of the invention to be performed. Where the target nucleic acids are RNA, the RNA can be reversed transcribed into cDNA by standard methods known in the art and as described in Sambrook, J., Fritsch, E. F., and Maniatis, T., *Molecular Cloning: A Laboratory Manual*. Cold Spring Harbor Laboratory Press, NY, Vol. 1, 2, 3 (1989), for example. The cDNA can then be analyzed according to the methods of the invention.

Target Nucleic Acids

Any target nucleic acid that can be tagged in an encoding reaction of the invention (described herein) can be detected using the methods of the invention. In typical embodiments, at least some nucleotide sequence information will be known for the target nucleic acids. For example, if the encoding reaction employed is PCR, sufficient sequence information is generally available for each end of a given target nucleic acid to permit design of suitable amplification primers.

The targets can include, for example, nucleic acids associated with pathogens, such as viruses, bacteria, protozoa, or fungi; RNAs, e.g., those for which over- or under-expression is indicative of disease, those that are expressed in a tissue- or developmental-specific manner; or those that are induced by particular stimuli; genomic DNA, which can be analyzed for specific polymorphisms (such as SNPs), alleles, or haplotypes, e.g., in genotyping. Of particular interest are genomic DNAs that are altered (e.g., amplified, deleted, and/or mutated) in genetic diseases or other pathologies; sequences that are associated with desirable or undesirable traits; and/or sequences that uniquely identify an individual (e.g., in forensic or paternity determinations).

Primer Design

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer, and where a probe is employed, proximity of the probe annealing site to the primer annealing site and ratio of primer:probe concentration. For example, depending on the complexity of the target nucleic acid sequence, an oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art knows how to select appropriate primer pairs to amplify the target nucleic acid of interest.

For example, PCR primers can be designed by using any commercially available software or open source software, such as Primer3 (see, e.g., Rozen and Skaletsky (2000) *Meth. Mol. Biol.,* 132: 365-386; www.broad.mit.edu/node/1060, and the like) or by accessing the Roche UPL website. The amplicon sequences are input into the Primer3 program with the UPL probe sequences in brackets to ensure that the Primer3 program will design primers on either side of the bracketed probe sequence.

Primers may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; the solid support method of U.S. Pat. No. 4,458, 066 and the like, or can be provided from a commercial source.

Primers may be purified by using a Sephadex column (Amersham Biosciences, Inc., Piscataway, N.J.) or other methods known to those skilled in the art. Primer purification may improve the sensitivity of the methods of the invention.

Microfluidic Devices

In certain embodiments, any of the methods of the invention can be carried out using a microfluidic device. In illustrative embodiments, a matrix-type microfluidic device is one that allows the simultaneous combination of a plurality of substrate solutions with reagent solutions in separate isolated reaction chambers. It will be recognized, that a substrate solution can comprise one or a plurality of substrates and a reagent solution can comprise one or a plurality of reagents. For example, the microfluidic device can allow the simultaneous pair-wise combination of a plurality of different amplification primers and samples. In certain embodiments, the device is configured to contain a different combination of primers and samples in each of the different chambers. In various embodiments, the number of separate reaction chambers can be greater than 50, usually greater than 100, more often greater than 500, even more often greater than 1000, and sometimes greater than 5000, or greater than 10,000.

In particular embodiments, the matrix-type microfluidic device is a Dynamic Array ("DA") microfluidic device. A DA microfluidic device is a matrix-type microfluidic device designed to isolate pair-wise combinations of samples and reagents (e.g., amplification primers, detection probes, etc.) and suited for carrying out qualitative and quantitative PCR reactions including real-time quantitative PCR analysis. In some embodiments, the DA microfluidic device is fabricated, at least in part, from an elastomer. DAs are described in PCT publication WO05107938A2 (Thermal Reaction Device and Method For Using The Same) and US Pat. Publication US20050252773A1, both incorporated herein by reference in their entireties for their descriptions of DAs. DAs may incorporate high-density matrix designs that utilize fluid communication vias between layers of the microfluidic device to weave control lines and fluid lines through the device and between layers. By virtue of fluid lines in multiple layers of an elastomeric block, high density reaction cell arrangements are possible. Alternatively DAs may be designed so that all of the reagent and sample channels are in the same elastomeric layer, with control channels in a different layer.

U.S. Patent Publication No. 2008/0223721 and PCT Publication No. WO 05/107938A2 describe illustrative matrix-type devices that can be used to practice the methods described herein. FIG. 21 of the latter is reproduced as FIG. 1 and shows an illustrative matrix design having a first elastomeric layer 2110 (1st layer) and a second elastomeric layer 2120 (2d layer) each having fluid channels formed therein. For example, a reagent fluid channel in the first layer 2110 is connected to a reagent fluid channel in the second layer 2120 through a via 2130, while the second layer 2120 also has sample channels therein, the sample channels and the reagent channels terminating in sample and reagent chambers 2180, respectively. The sample and reagent chambers 2180 are in fluid communication with each other through an interface channel 2150 that has an interface valve 2140 associated therewith to control fluid communication between each of the chambers 2180 of a reaction cell 2160. In use, the interface is first closed, then reagent is introduced into the reagent channel from the reagent inlet and sample is introduced into the sample channel through the sample inlet; containment valves 2170 are then closed to isolate each reaction cell 2160 from other reaction cells 2160. Once the reaction cells 2160 are isolated, the interface valve 2140 is opened to cause the sample chamber and the reagent chamber to be in fluid communication with each other so that a desired reaction may take place. It will be apparent from this (and the description in WO 05/107938A2) that the DA may be used for reacting M number of different samples with N number of different reagents.

Although the DAs described above in WO 05/107938 are well suited for conducting the methods described herein, the invention is not limited to any particular device or design. Any device that partitions a sample and/or allows independent pair-wise combinations of reagents and sample may be used. U.S. Patent Publication No. 20080108063 (which is hereby incorporated by reference it its entirety) includes a diagram illustrating the 48.48 Dynamic Array, a commercially available device available from Fluidigm Corp. (South San Francisco Calif.). It will be understood that other configurations are possible and contemplated such as, for example, 48×96; 96×96; 30×120; etc.

In specific embodiments, the microfluidic device can be a Digital Array microfluidic device, which is adapted to perform digital amplification. Such devices can have integrated channels and valves that partition mixtures of sample and reagents into nanoliter volume reaction chambers. In some embodiments, the Digital Array microfluidic device is fabricated, at least in part, from an elastomer. Illustrative Digital Array microfluidic devices are described in copending U.S. Applications owned by Fluidigm, Inc. One illustrative embodiment has 12 input ports corresponding to 12 separate sample inputs to the device. The device can have 12 panels, and each of the 12 panels can contain 765 6 mL reaction chambers with a total volume of 4.59 µL per panel. Microfluidic channels can connect the various reaction chambers on the panels to fluid sources. Pressure can be applied to an accumulator in order to open and close valves connecting the reaction chambers to fluid sources. In illustrative embodiments, 12 inlets can be provided for loading of the sample reagent mixture. 48 inlets can be used to provide a source for reagents, which are supplied to the microfluidic device when pressure is applied to accumulator. Additionally, two or more inlets can be provided to provide hydration to the microfluidic device. Hydration inlets are in fluid communication with the device to facilitate the control of humidity associated with the reaction chambers. As will be understood by one of skill in the art, some elastomeric materials that can utilized in the fabrication of the device are gas permeable, allowing evaporated gases or vapor from the reaction chambers to pass through the elastomeric material into the surrounding atmosphere. In a particular embodiment, fluid lines located at peripheral portions of the device provide a shield of hydration liquid, for example, a buffer or master mix, at peripheral portions of the microfluidic device surrounding the panels of reaction chambers, thus reducing or preventing evaporation of liquids present in the reaction chambers. Thus, humidity at peripheral portions of the device can be increased by adding a volatile liquid, for example water, to hydration inlets. In a specific embodiment, a first inlet is in fluid communication with the hydration fluid lines surrounding the panels on a first side of the device and the second inlet is in fluid communication with the hydration fluid lines surrounding the panels on the other side of the device.

While the Digital Array microfluidic devices are well-suited for carrying out the digital amplification methods described herein, one of ordinary skill in the art would recognize many variations and alternatives to these devices. The microfluidic device which is the 12.765 Digital Array commercially available from Fluidigm Corp. (South San Francisco, Calif.), includes 12 panels, each having 765 reaction chambers with a volume of 6 nL per reaction chamber. However, this geometry is not required for digital amplification methods. The geometry of a given Digital Array microfluidic device will depend on the particular application. Additional description related to devices suitable for use in the methods described herein is provided in U.S. Patent Application Publication No. 2005/0252773, incorporated herein by reference for its disclosure of Digital Array microfluidic devices.

In certain embodiments, the methods described herein can be performed using a microfluidic device that provides for recovery of reaction products. Such devices are described in detail in copending U.S. Application No. 61/166,105, filed Apr. 2, 2009, which is hereby incorporated by reference in its entirety and specifically for its description of microfluidic devices that permit reaction product recovery and related methods. For example, a digital PCR method for calibrating DNA samples prior to sequencing can be preformed on such devices, permitting recovery of amplification products, which can then serve as templates for DNA sequencing.

Fabrication methods using elastomeric materials and methods for design of devices and their components have been described in detail in the scientific and patent literature. See, e.g., Unger et al., 2000, Science 288:113-16; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic systems including three-dimensionally arrayed channel networks); U.S. Patent Application Publication Nos. 2004/0115838; 20050072946; 20050000900; 20020127736; 20020109114; 20040115838; 20030138829; 20020164816; 20020127736; and 20020109114; PCT Publication Nos. WO 2005/084191; WO05030822A2; and WO 01/01025; Quake & Scherer, 2000, "From micro to nanofabrication with soft materials" Science 290: 1536-40; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23, Hong et al, 2004, "A nanoliter-scale nucleic acid processor with parallel architecture" Nature Biotechnology 22:435-39.

According to certain embodiments of the invention, the detection and/or quantification of one or more target nucleic acids from one or more samples may generally be carried out on a microfluidic device by obtaining a sample, optionally pre-amplifying the sample, and distributing aliquots of the pre-amplified sample into reaction chambers of a microfluidic device containing the appropriate buffers, primers, optional probe(s), and enzyme(s), subjecting these mixtures to amplification, and querying the aliquots for the presence of amplified target nucleic acids. The sample aliquots may have a volume of in the range of about 1 picoliter to about 500 nanoliters, in the range of about 100 picoliters to about 20 nanoliters, in the range of about 1 nanoliter to about 20 nanoliters, or in the range of about 5 nanoliters to about 15 nanoliters.

In certain embodiments, multiplex detection is carried out in individual amplification mixture, e.g., in individual reaction chambers of a matrix-type microfluidic device, which can be used to further increase the number of samples and/or targets that can be analyzed in a single assay or to carry out comparative methods, such as comparative genomic hybridization (CGH)-like analysis of multiple loci.

In specific embodiments, the assay usually has a dynamic range of at least 3 orders of magnitude, more often at least 4, at least 5, at least 6, at least 7, or at least 8 orders of magnitude.
Quantitative Real-Time PCR and Other Detection and Quantitation Methods Any method of detection and/or quantitation of nucleic acids can be used in the invention to detect amplification products. In one embodiment, PCR (polymerase chain reaction) is used to amplify and/or quantitate target nucleic acids. In a variation of this embodiment, digital PCR can be employed. In other embodiments, other amplification systems or detection systems are used, including, e.g., systems described in U.S. Pat. No. 7,118,910 (which is incorporated herein by reference in its entirety for its description of amplification/detection systems) and Invader assays; PE BioSystems). In particular embodiments, real-time quantitation methods are used. For example, "quantitative real-time PCR" methods can be used to determine the quantity of a target nucleic acid present in a sample by measuring the amount of amplification product formed during the amplification process itself.

Fluorogenic nuclease assays are one specific example of a real-time quantitation method that can be used successfully in the methods described herein. This method of monitoring the formation of amplification product involves the continuous measurement of PCR product accumulation using a dual-labeled fluorogenic oligonucleotide probe—an approach frequently referred to in the literature as the "TAQMAN® method." See U.S. Pat. No. 5,723,591; Heid et al., 1996, Real-time quantitative PCR Genome Res. 6:986-94, each incorporated herein by reference in their entireties for their descriptions of fluorogenic nuclease assays. It will be appreciated that while "TAQMAN® probes" are the most widely used for qPCR, the invention is not limited to use of these probes; any suitable probe can be used.

Other detection/quantitation methods that can be employed in the present invention include FRET and template extension reactions, molecular beacon detection, Scorpion detection, Invader® detection, and padlock probe detection.

FRET and template extension reactions utilize a primer labeled with one member of a donor/acceptor pair and a nucleotide labeled with the other member of the donor/acceptor pair. Prior to incorporation of the labeled nucleotide into the primer during a template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, Nat. Biotechnol. 16:359-63; Tyagi, and Kramer, 1996, Nat. Biotechnology 14:303-308; and Tyagi, et al., 1998, Nat. Biotechnol. 16:49-53 (1998).

The Scorpion detection method is described, for example, by Thelwell et al. 2000, Nucleic Acids Research, 28:3752-3761 and Solinas et al., 2001, "Duplex Scorpion primers in SNP analysis and FRET applications" Nucleic Acids Research 29:20. Scorpion primers are fluorogenic PCR primers with a probe element attached at the 5'-end via a PCR stopper. They are used in real-time amplicon-specific detection of PCR products in homogeneous solution. Two different formats are possible, the "stem-loop" format and the "duplex" format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

INVADER® assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time, the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., *Advances in Nucleic Acid and Protein Analysis* 3826:117-125, 2000) and U.S. Pat. No. 6,706,471.

Padlock probes (PLPs) are long (e.g., about 100 bases) linear oligonucleotides. The sequences at the 3' and 5' ends of the probe are complementary to adjacent sequences in the target nucleic acid. In the central, noncomplementary region of the PLP there is a "tag" sequence that can be used to identify the specific PLP. The tag sequence is flanked by universal priming sites, which allow PCR amplification of the tag. Upon hybridization to the target, the two ends of the PLP oligonucleotide are brought into close proximity and can be joined by enzymatic ligation. The resulting product is a circular probe molecule catenated to the target DNA strand. Any unligated probes (i.e., probes that did not hybridize to a target) are removed by the action of an exonuclease. Hybridization and ligation of a PLP requires that both end segments recognize the target sequence. In this manner, PLPs provide extremely specific target recognition.

The tag regions of circularized PLPs can then be amplified and resulting amplicons detected. For example, TAQMAN® real-time PCR can be carried out to detect and quantitate the amplicon. The presence and amount of amplicon can be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8.

In particular embodiments, fluorophores that can be used as detectable labels for probes include, but are not limited to, rhodamine, cyanine 3 (Cy 3), cyanine 5 (Cy 5), fluorescein, VIC™, LIZ™, TAMRA™, 5-FAM™, 6-FAM™, and Texas Red labels (Molecular Probes). (VIC™, Liz™, VIC™, 5-FAM™, 6-FAMF™ are all available from Applied Biosystems, Foster City, Calif.).

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670.

In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In particular embodiments, combined thermal cycling and fluorescence detecting devices can be used for precise quantification of target nucleic acids. In some embodiments, fluorescent signals can be detected and displayed during and/or after one or more thermal cycles, thus permitting monitoring of amplification products as the reactions occur in "real-time." In certain embodiments, one can use the amount of amplification product and number of amplification cycles to calculate how much of the target nucleic acid sequence was in the sample prior to amplification.

According to some embodiments, one can simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid.

According to certain embodiments, one can employ an internal standard to quantitate the amplification product indicated by the fluorescent signal. See, e.g., U.S. Pat. No. 5,736, 333.

By acquiring fluorescence over different temperatures, it is possible to follow the extent of hybridization. Moreover, the temperature-dependence of PCR product hybridization can be used for the identification and/or quantification of PCR products. Accordingly, the methods described herein encompass the use of melting curve analysis in detecting and/or quantifying amplicons. Melting curve analysis is well known and is described, for example, in U.S. Pat. Nos. 6,174,670; 6,472,156; and 6,569,627, each of which is hereby incorporated by reference in its entirety, and specifically for its description of the use of melting curve analysis to detect and/or quantify amplification products. In illustrative embodiments, melting curve analysis is carried out using a double-stranded DNA dye, such as SYBR® Green dye, PICOGREEN® dye (Molecular Probes, Inc., Eugene, Oreg.), ethidium bromide, and the like (see Zhu et al., 1994, Anal. Chem. 66:1941-48).

In various embodiments, employing preamplification, the number of preamplification cycles is sufficient to add one or more nucleotide tags to the target nucleotide sequences, so that the relative copy numbers of the tagged target nucleotide sequences is substantially representative of the relative copy numbers of the target nucleic acids in the sample. For example, preamplification can be carried out for 2-20 cycles to introduce the sample-specific or set-specific nucleotide tags. In other embodiments, detection is carried out at the end of exponential amplification, i.e., during the "plateau" phase, or endpoint PCR is carried out. In this instance, preamplification will normalize amplicon copy number across targets and across samples. In various embodiments, preamplification and/or amplification can be carried out for about: 2, 4, 10, 15, 20, 25, 30, 35, or 40 cycles or for a number of cycles falling within any range bounded by any of these values.

If desired, tagged target nucleotide sequences generated as described herein may be analyzed by DNA sequencing. Many current DNA sequencing techniques rely on "sequencing by synthesis." These techniques entail library creation, massively parallel PCR amplification of library molecules, and sequencing. Library creation starts with conversion of sample nucleic acids to appropriately sized fragments, ligation of adaptor sequences onto the ends of the fragments, and selection for molecules properly appended with adaptors. The presence of the adaptor sequences on the ends of the library molecules enables amplification of random-sequence inserts. The above-described methods for tagging nucleotide sequences can be substituted for ligation, to introduce adaptor sequences.

In particular embodiments, the number of library DNA molecules produced in the massively parallel PCR step is low enough that the chance of two molecules associating with the same substrate, e.g. the same bead (in 454 DNA sequencing) or the same surface patch (in Solexa DNA sequencing) is low, but high enough so that the yield of amplified sequences is sufficient to provide a high throughput in automated sequencing. After suitable adaptor sequences are introduced, as discussed above, digital PCR can be employed to calibrate the number of library DNA molecules prior to sequencing by synthesis.

Labeling Strategies

Any suitable labeling strategy can be employed in the methods of the invention. Where the assay mixture is aliquoted, and each aliquot is analyzed for presence of a single amplification product, a universal detection probe can be employed in the amplification mixture. In particular embodiments, real-time PCR detection can be carried out using a universal qPCR probe. Suitable universal qPCR probes include double-stranded DNA dyes, such as SYBR® Green dye, PICOGREEN® dye (Molecular Probes, Inc., Eugene, Oreg.), ethidium bromide, and the like (see Zhu et al., 1994, *Anal. Chem.* 66:1941-48). Suitable universal qPCR probes also include sequence-specific probes that bind to a nucleotide sequence present in all amplification products. Binding sites for such probes can be conveniently introduced into the tagged target nucleotide sequences during preamplification (in embodiments employing preamplification) and/or into amplification products during amplification.

Alternatively, one or more target-specific qPCR probes (i.e., specific for a target nucleotide sequence to be detected) is employed in the amplification mixtures to detect amplification products. Target-specific probes could be useful, e.g., when only a few target nucleic acids are to be detected in a large number of samples. For example, if only three targets were to be detected, a target-specific probe with a different fluorescent label for each target could be employed. By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Removal of Undesired Reaction Components

It will be appreciated that reactions involving complex mixtures of nucleic acids in which a number of reactive steps are employed can result in a variety of unincorporated reaction components, and that removal of such unincorporated reaction components, or reduction of their concentration, by any of a variety of clean-up procedures can improve the efficiency and specificity of subsequently occurring reactions. For example, it may be desirable, in some embodiments, to remove, or reduce the concentration of preamplification primers prior to carrying out the amplification steps described herein.

In certain embodiments, the concentration of undesired components can be reduced by simple dilution. For example, preamplified samples can be diluted about 2-, 5-, 10-, 50-, 100-, 500-, 1000-, 5000-, or 10,000-fold prior to amplification to improve the specificity of the subsequent amplification step. Those of skill in the art appreciate that the dilution can also fall within a range bounded by any of they above values (e.g., about 100-fold to about 1000-fold).

In some embodiments, undesired components can be removed by a variety of enzymatic means. Examples of suitable enzymatic means include enzymes that digest single-stranded nucleic acids, such as *E. coli* exonuclease I. Excess dNTPs left over from the amplification reaction can be "removed" by treatment with shrimp alkaline phosphatase (SAP), which removes the phosphate groups from dNTPs. Uracil N-glycosylase (UNG) (AMPERASE® Uracil N-glycosylase (UNG) from Applied Biosystems, Inc., Foster City, Calif.), can be used to prevent unwanted carry-over primers from an initial amplification reaction in which the primers contained dUTP, instead of dTTP. UNG degrades U-containing primers.

Alternatively, unreacted primers and dNTPs can be removed by column chromatography. For example, gel filtration over Sephadex can be employed for this purpose.

In particular embodiments, clean-up includes selective immobilization of nucleic acids. For example, desired nucleic acids can be preferentially immobilized on a solid support. In an exemplary embodiment, photo-biotin is attached to desired nucleic acid, and the resulting biotin-labeled nucleic acids immobilized on a solid support comprising an affinity-moiety binder such as streptavidin. Alternatively, unwanted nucleic acids can be immobilized on a solid support and desired nucleic acids harvested by washing.

Use of Blocking Agents During Amplification

In certain embodiments, amplification can be carried out in the presence of a blocking agent to increase specific amplification of the target nucleic acid. Such an agent can suppress background noise generated during amplification, increase specific amplification of one or more target nucleic acids, and/or improve the quality of amplification (e.g., possibly by improving the efficiency of amplification).

Blocking agents can be employed in any amplification reaction, for example, where a genomic DNA sample is being preamplified or amplified. Genomic DNA contains repetitive nucleotide sequences to which primers may non-specifically hybridize, which may increase background noise and compete with target nucleic acids for primers. The inclusion of a blocking agent in the amplification reaction mixture increases specific amplification of the target nucleic acid. In various embodiments, the increase in specific amplification can be about 10 percent, about 25 percent, about 50 percent, about 75 percent, about 100 percent, about 150 percent, about 200 percent, about 250 percent, about 300 percent, about 350 percent, about 400 percent, about 450 percent, or about 500 percent of the amplification observed in the absence of blocking agent. Without being bound by a particular theory, it is believed that the blocking may act by hybridizing to repetitive sequences in the genomic DNA sample.

Blocking agents also find particular utility in multiplex amplification reactions using genomic DNA or other types of nucleic acid samples. In multiplex amplification, the presence of multiple primers in the amplification reaction mixture can increase signal attributable to non-specific hybridization of the multiple primers. The inclusion of a blocking agent may suppress this signal.

In an illustrative embodiment, a nucleic acid blocking agent, such as tRNA, is employed as a blocking agent in an amplification reaction, such as, e.g., PCR. Other blocking agents can include degenerate oligonucleotide primers, repetitive DNA, BSA, or glycogen.

The blocking agent should present in an amount to increase specific amplification of the target nucleic acid. In certain embodiments, the blocking agent is present at a concentration in the range of about 0.1 µg/µl to about 40 µg/µl. In specific embodiments, the blocking agent concentration can be about 0.1, about 0.2, about 0.3, about 0.4, about 0.5, about 0.6, about 0.7, about 1, about 2, about 3, about 4, about 5, about 6, about 7, about 8, about 9, about 10, about 15, about 20, about 25, about 30, about 35, or about 40 µg/µl of the preamplification or amplification reaction mixture or can be any range having any of these values as endpoints (e.g., about 1 µg/µl to about 5 µg/µl). Suitable amounts can be also determined empirically, as shown in Example 4.

In an illustrative embodiment, tRNA is employed as a blocking agent at a concentration in the range of about 1 µg/µl to about 5 µg/µl, e.g., about 2 or 3 µg/µl.

Applications

The methods of the invention are applicable to any technique aimed at detecting the presence or amount of one or more target nucleic acids in a nucleic acid sample. Thus, for example, these methods are applicable to identifying the presence of particular polymorphisms (such as SNPs), alleles, or haplotypes, or chromosomal abnormalities, such as amplifications, deletions, or aneuploidy. The methods may be employed in genotyping, which can be carried out in a number of contexts, including diagnosis of genetic diseases or disorders, pharmacogenomics (personalized medicine), quality control in agriculture (e.g., for seeds or livestock), the study and management of populations of plants or animals (e.g., in aquaculture or fisheries management or in the determination of population diversity), or paternity or forensic identifications. The methods of the invention can be applied to the identification of sequences indicative of particular conditions or organisms in biological or environmental samples. For example, the methods can be used to identify pathogens, such as viruses, bacteria, and fungi). The methods can also be used to characterize environments or microenvironments, e.g., to characterize the microbial species in the human gut.

These methods can also be employed to determine DNA or RNA (e.g., mRNA, miRNA) copy number. Determinations of aberrant DNA copy number in genomic DNA is useful, for example, in the diagnosis and/or prognosis of genetic defects and diseases, such as cancer. Determination of RNA "copy number," i.e., expression level is useful for expression monitoring of genes of interest, e.g., in different individuals, tissues, or cells under different conditions (e.g., different external stimuli or disease states) and/or at different developmental stages. Primers can also function as probes.

In addition, the methods can be employed to prepare nucleic acid samples for further analysis, such as, e.g., DNA sequencing.

Finally, nucleic acid samples can be tagged as a first step, prior subsequent analysis, to reduce the risk that mislabeling or cross-contamination of samples will compromise the results. For example, any physician's office, laboratory, or hospital could tag samples immediately after collection, and the tags could be confirmed at the time of analysis. Similarly, samples containing nucleic acids collected at a crime scene could be tagged as soon as practicable, to ensure that the samples could not be mislabeled or tampered with. Detection of the tag upon each transfer of the sample from one party to another could be used to establish chain of custody of the sample.

Kits

Kits according to the invention include one or more reagents useful for practicing one or more assay methods of the invention. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits according to the invention generally include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1

"More Samples" Chemistry Using Unique Tags for Every Primer

This example provides an exemplary protocol for carrying out an assay method of the invention to measure gene expression of 16 targets in up to 144 samples using a 48.48 Dynamic Array available from Fluidigm Corporation, South San Francisco, Calif.

To increase the sample throughput for gene expression using a dynamic array without chip design change, we developed a new protocol to measure gene expression in more than 48 samples on less than 48 (i.e. 16) targets using one M48 chip. This protocol involved tagging, combining and real-time PCR steps. For proof of concept only 3 target genes were encoded and analyzed.

During the Tagging step, cDNA samples were divided into 3 separate groups. The forward and reverse primers of 3 targets (GAPDH, LDH1, HPRT) for the three groups were synthesized with unique tag sequences appended to the 5' end of the primers (total of 18 different tags) respectively. In this way, each pair of tags defines a specific target amplified and tagged with reagents for a specific group.

Each group-specific set of tagged primers were pooled together with 33 other, non-tagged gene expression mixes to simulate high complexity in the preamplification.

In the tagging step (preamplification of targets with the tagged primers), the 3 separate groups c DNA samples (Standard cDNA, eight titrations 4× diluted, from 5 ng to 0.3 pg) were amplified in a 5 µl reaction containing 2.5 µl of 2× Preamp master mix (Applied Biosystems), 1 µl of the multiplex tagging primer mix (one separate mix per sample group), 1 µl cDNA and 0.5 µl DNA-free water. PCR was performed with an initial 15 min at 95° C., followed by 14 cycles of a 2-step amplification profile of 15 sec at 95° C. for denaturation, 4 min at 60° C. for annealing and extension. The PCR products were diluted 100-fold with DNA suspension buffer (low EDTA TE from TEKnova). Then the PCR products from the 3 groups were combined, with every combined sample having one sample from each of the 3 tagging groups. As a comparison, samples from different tag groups were analyzed individually by quantitative real-time PCR. Also, the analysis was performed in parallel with untagged primers and without mixing samples.

The combined samples were analyzed by real-time quantitative PCR on a dynamic array chip. The 10× assay mix was prepared for each tag pair with the corresponding TAQMAN® probes in a 5 µl reaction containing 2 µM TAQMAN® probe, 9 µM of two tag-specific primers and 1× assay loading reagent (Fluidigm). A 5 µL sample mix was prepared for each 2.5 µL of (combined or individual) samples, containing 1× TAQMAN® Universal Master Mix (Applied Biosystems, Foster City, Calif.), 1×DA Sample Loading Reagent. A standard TAQMAN® gene expression was performed as mentioned above on the dynamic array chip.

The $\Delta\Delta C_T$ for different samples of HPRT cDNA and GAPDH cDNA was determined against a reference sample (ABC at relative concentration 0.063, grey background). Samples from three groups A, B and C were not mixed ("individual"), mixed with samples of the same concentration ("ABC") or mixed with samples of different concentration ("A fixed"). Relative concentration refers to the amount of cDNA added to the tagging reaction ("1.000"=5 nano gram). $\Delta\Delta C_T$ values are listed for samples being analyzed with group A, B and C specific tag primers respectively and with untagged primers, i.e. the primers with the sequence of the target specific portion of the pre-amplification primers. The results are shown in Table 1.

TABLE 1

| Sample mix | rConc | A-tag-primers | B-tag-primers | C-tag-primers | Untagged primers |
|---|---|---|---|---|---|
| individual | 0.016 | −0.1 | −0.2 | −0.4 | 0.1 |
| individual | 0.063 | −0.1 | −0.9 | 0.1 | 0.3 |

TABLE 1-continued

| Sample mix | rConc | A-tag-primers | B-tag-primers | C-tag-primers | Untagged primers |
|---|---|---|---|---|---|
| individual | 0.250 | 0.6 | −0.5 | −0.1 | 0.1 |
| individual | 1.000 | 0.1 | −0.5 | −0.2 | 0.1 |
| ABC | 0.016 | −0.72 | −0.79 | −0.41 | 0.93 |
| ABC | 0.063 | 0.0 | 0.0 | 0.0 | 0.0 |
| ABC | 0.250 | 0.2 | −0.6 | 0.0 | 0.2 |
| ABC | 1.000 | 0.2 | −0.4 | −0.2 | 0.0 |
| A fixed | 0.016 | 0.7 | −0.5 | 0.5 | 0.5 |
| A fixed | 0.063 | 0.4 | −0.8 | 0.1 | 0.2 |
| A fixed | 0.250 | 0.1 | −0.5 | −0.3 | −0.2 |
| A fixed | 1.000 | 0.7 | −0.6 | −0.2 | 0.0 |
| | AVG | 0.2 | −0.5 | −0.1 | 0.2 |
| | STDEV | 0.39 | 0.24 | 0.24 | 0.29 |

Example 2

"More Samples" Chemistry for Genotyping

This example provides an exemplary protocol for carrying out an assay method of the invention to genotype 16 single nucleotide polymorphsims ("SNPs") in 144 samples (including no template controls ("NTCs")) using a 48.48 Dynamic Array available from Fluidigm Corporation, South San Francisco, Calif.

Figure 4:
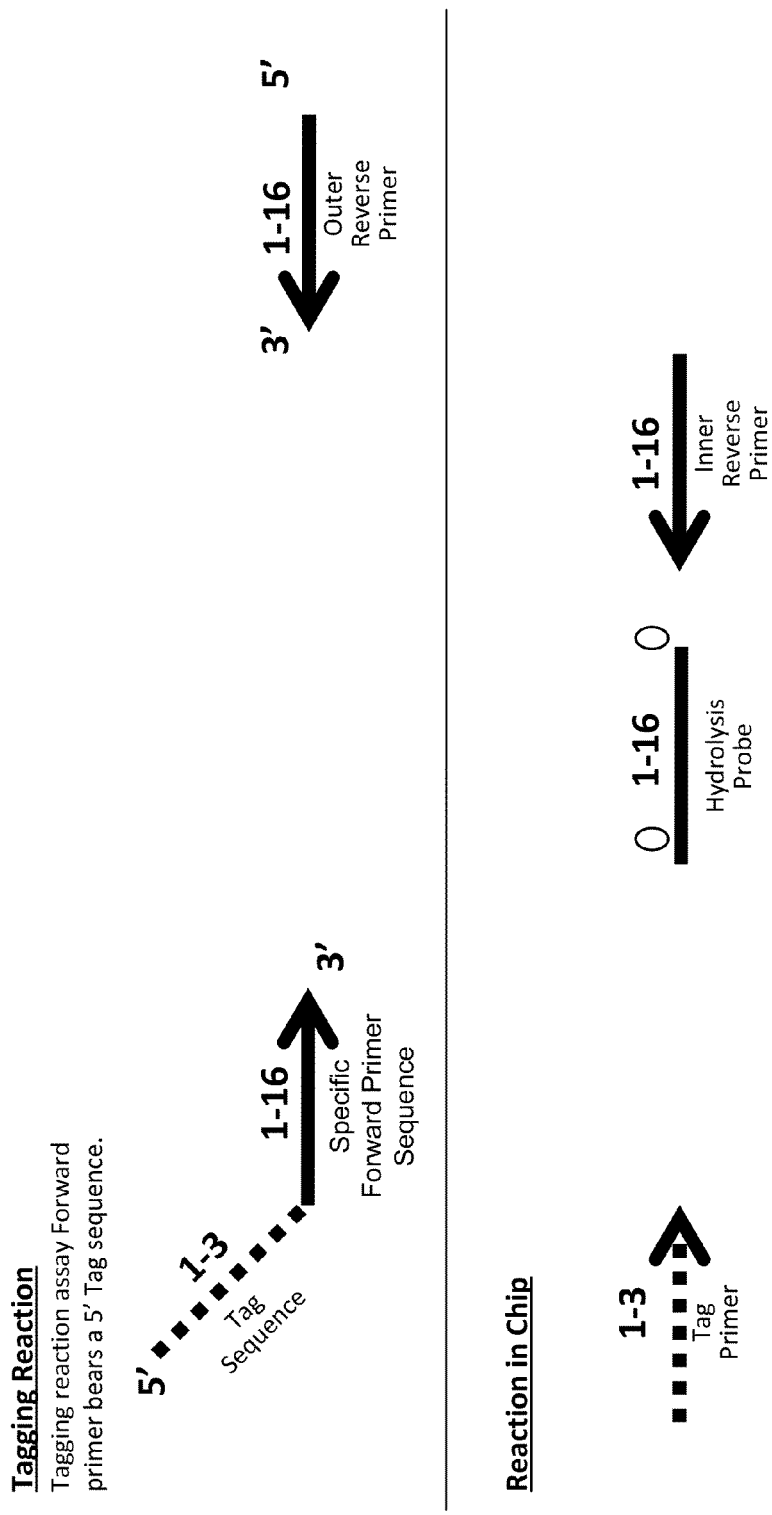
FIG. 4 shows an illustrative setup for analyzing multiple target nucleic acids in multiple samples as in, e.g., the gene expression study of Example 3. This study employed 3 tag groups (1-3) targeting 16 loci. Three sets of 16 forward primers for amplifying 16 cDNAs were synthesized. If each group tags 48 individuals, and 1 sample from each tag group is combined, 144 samples can be simultaneously analyzed. Before the off-chip tagging reaction, samples were divided into each of the 3 tag sets. Each group of 48 samples bears either Tag sequence 1, 2, or 3 on the 5' termini of the forward primers. Tagging reactions employ an assay-specific tagged primer and an outer reverse primer. On chip, a nested reverse primer can be used. In the example for gene expression, a single hydrolysis probe is shown.
Figure 5:
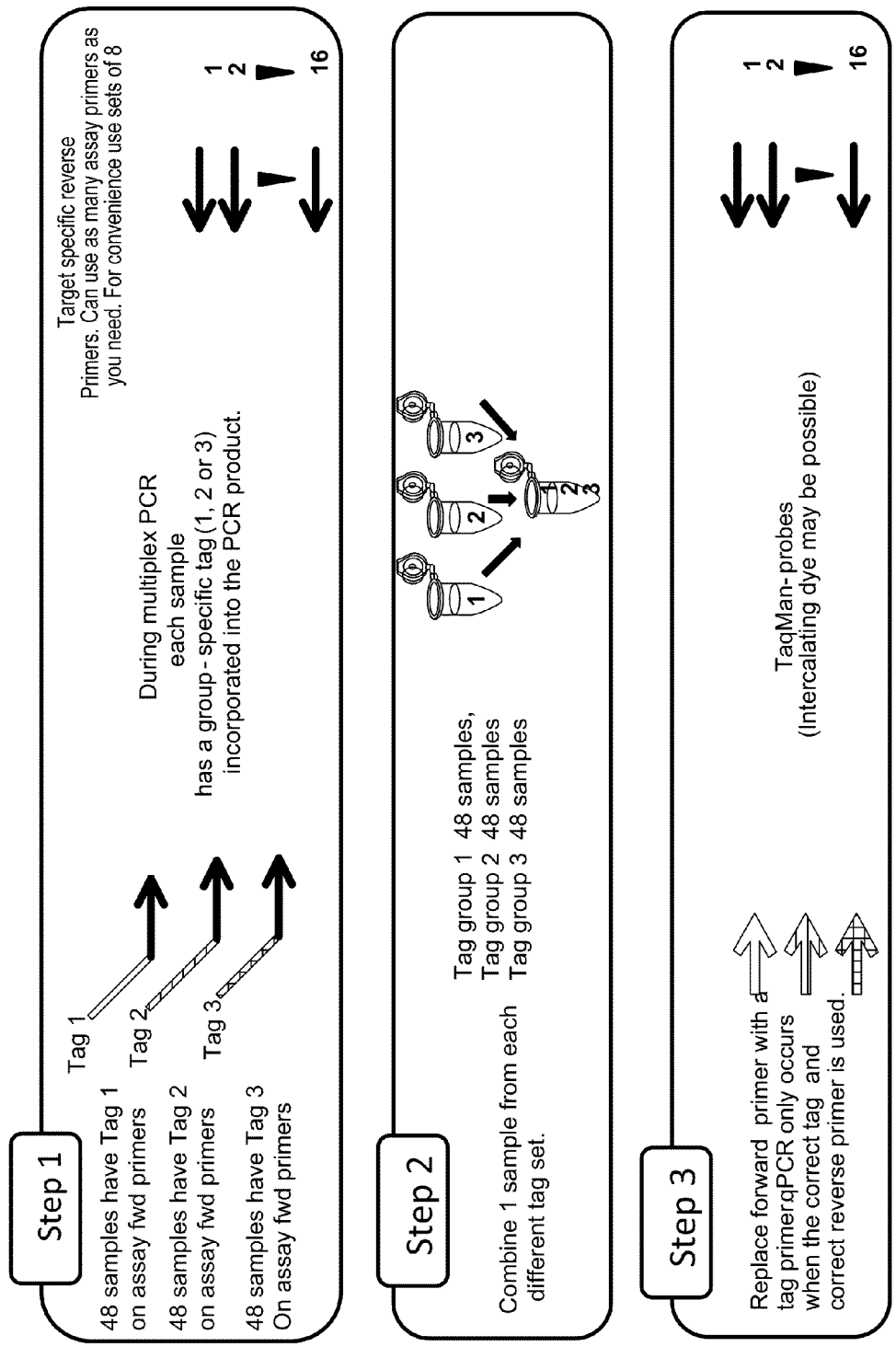
FIG. 5 shows an illustrative generic setup for analyzing multiple target nucleic acids in multiple samples. For example, allele-specific probes (genotyping) or a single probe (gene expression) can be used. After combining samples, residual primers can be removed using EXOSAP-IT® PCR product clean-up (USB) prior to the PCR step.
Figure 6:
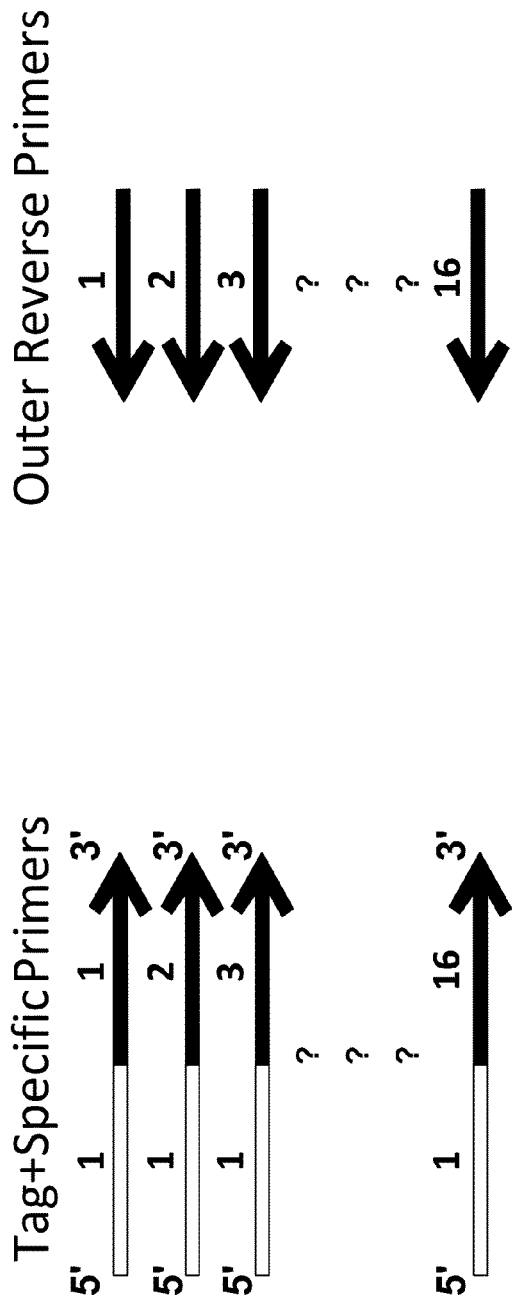
FIG. 6 shows an illustrative generic setup for analyzing multiple target nucleic acids in multiple samples, in this case, 16 assays are performed on 144 samples. Three sets of 16 forward primers for amplifying 16 loci are synthesized. Each tag set also bears Tag sequence 1, 2, or 3 on the 5' primer termini. During the off-chip tagging reaction, 32 primers consisting of 16 forward assay primers with tag sequence 1 and 16 reverse assay-specific reverse primers are used. Assay-specific tag primers bearing a different 5' tag sequence (Tag 2) and the same sequence reverse primers are used to tag the next set of samples. This is also performed with Tag type 3 and another set of samples. After tagging 48× samples with tag set 1, 48× samples with tag set 2, and 48× samples with tag set 3, one sample per each tag set is combined. This generates 48 mixed samples, and efficient PCR amplification of a specific target from one of the mixed samples (but not the other two) will only occur when the correct tag primer and target specific reverse primer are added to the pooled samples.

To further increase the sample throughput for genotyping using a dynamic array without chip design change, we developed a new protocol to genotype more than 48 samples on less than 48 (i.e. 16) SNPs using one 48.48CS chip. This protocol involved tagging, combining, and genotyping steps (see FIGS. 4, 5, and 6). During the tagging step, DNA samples were divided into 3 separate groups with 47 individuals each (plus one space for NTC). Three sets of 16 5' forward primers for amplifying 16 SNPs were synthesized. Each set had a different Tag sequence appended to the 5' end of the primers respectively. Each 16 forward primers with the same Tag attached were pooled together and mixed with the 16 SNP specific 3' reverse primers to make multiplex tagging primer mix, one for each Tag.

In the tagging step, the 3 separate groups of 47 tomato DNA samples were amplified in a 5 µl reaction containing 2.5 µl of 2× Multiplex PCR Master Mix (Qiagen), 1 µl of the multiplex tagging primer mix (one separate Tag per sample group), 1 µl DNA at 60 ng/uL and 0.5 µl DNA-free water. PCR was performed with an initial 15 min at 95° C., then followed by 14 cycles of a 2-step amplification profile of 15 sec at 95° C. for denaturation, 4 min at 60° C. for annealing and extension. The PCR products were diluted 100-fold with DNA suspension buffer (low EDTA TE from TEKnova). Then the 47 PCR products from the 3 groups were combined into one group of 47 samples, with every combined sample having one from each of the 3 Tagging groups.

Figure 2:
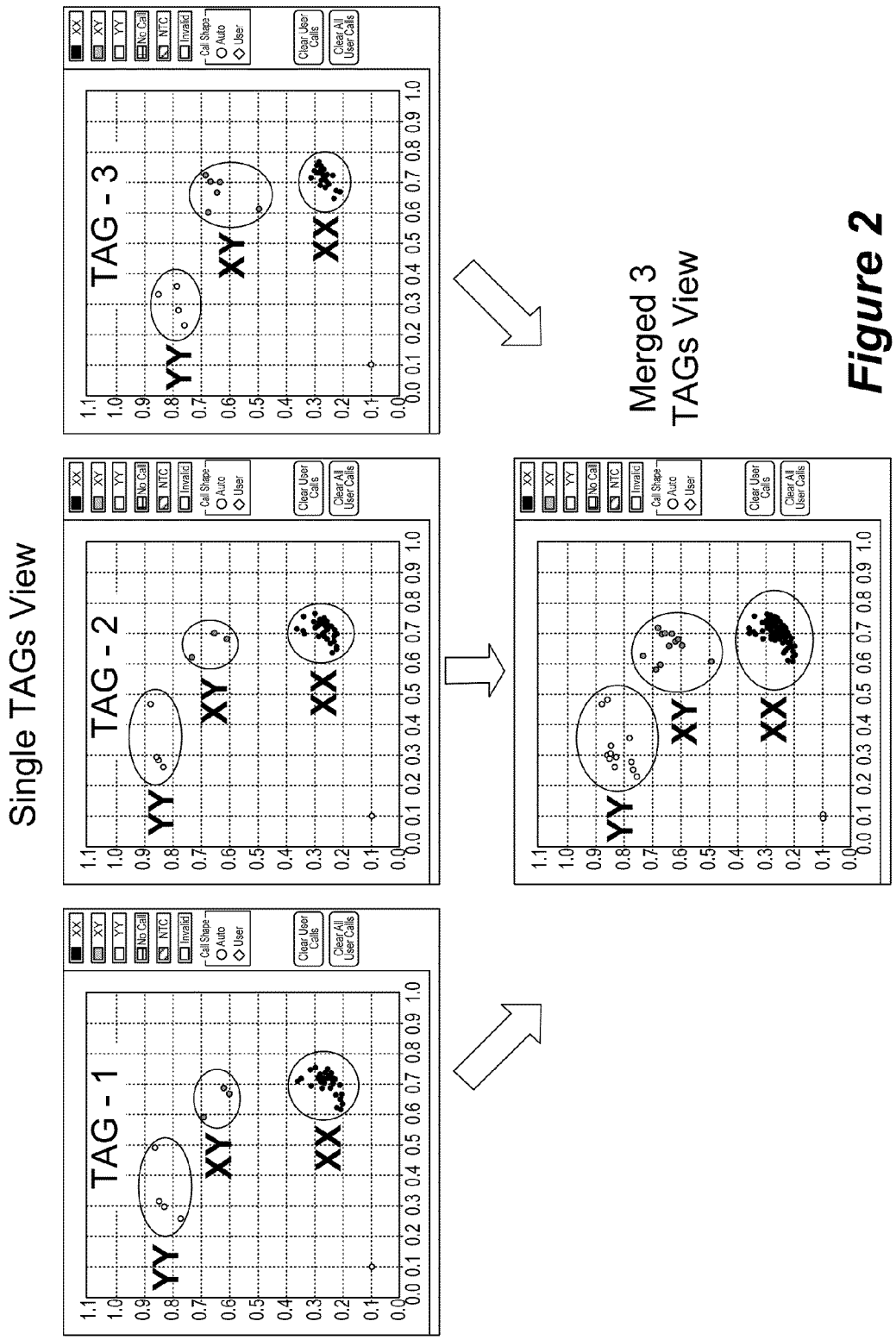
FIG. 2 shows a graphical depiction of the results of the application of a method of the invention for analyzing multiple target nucleic acids in multiple samples in a genotyping study (Example 2). Samples were amplified with forward primers bearing 3 different tag sequences. The results are shown in the Single TAG view allelograms (top images) labeled TAG—1, 2, and 3. All samples were clearly differentiated into (circled) homozygote XX, YY or heterozygote XY genotypes. Data from the merged genotypes of these allelograms are shown as "Merged 3".

The combined 47 samples plus one sample with DNA suspension buffer as negative control ("NTC") were genotyped on dynamic array chip. The 10× assay mix was prepared for each SNP individually in a 5 µl reaction containing 2 µM TAQMAN® probes (FAM™ and VIC™ labels), 9 µM of corresponding SNP specific reverse primers, 2.5×ROX™ (Invitrogen), 0.25% of Tween 20 and 9 µM of one of the 3 Tag primers (Tag-1 GTACGGTAGCAGAGA CTTGGTCTG (SEQ ID NO:1), Tag-2 GACTTAATGCTGC TTGAGACT-TGC (SEQ ID NO:21), and Tag-3 GACATCGT ACCT-GACTCAT CGCAC (SEQ ID NO:3)). And three 10× assay mixes were made for each SNP, one for each Tag. Total 48 assay mixes were made for the 16 SNPs, in 3 Tag groups. A 5

µL sample mix was prepared for each 2.5 µL of 1:100 diluted combined samples and NTC, containing 1× TAQMAN® Universal Master Mix (Applied Biosystems, Foster City, Calif.), 1× GT Sample Loading Reagent (Fluidigm PN 85000741), and 0.05 units/µL additional extra Taq-Gold polymerase (Applied Biosystems). A standard TAQMAN® genotyping was performed as mentioned above on dynamic array chip. The results are shown in FIGS. 2 and 3.

Example 3

"More Samples" Chemistry for qPCR Gene Expression Profiling

This example provides an exemplary protocol for carrying out an assay method of the invention to quantify the expression of 16 cDNAs in 36 serially diluted samples using a 96.96 DYNAMIC ARRAY® integrated fluidic circuit available from Fluidigm Corporation, South San Francisco, Calif.

Figure 7:
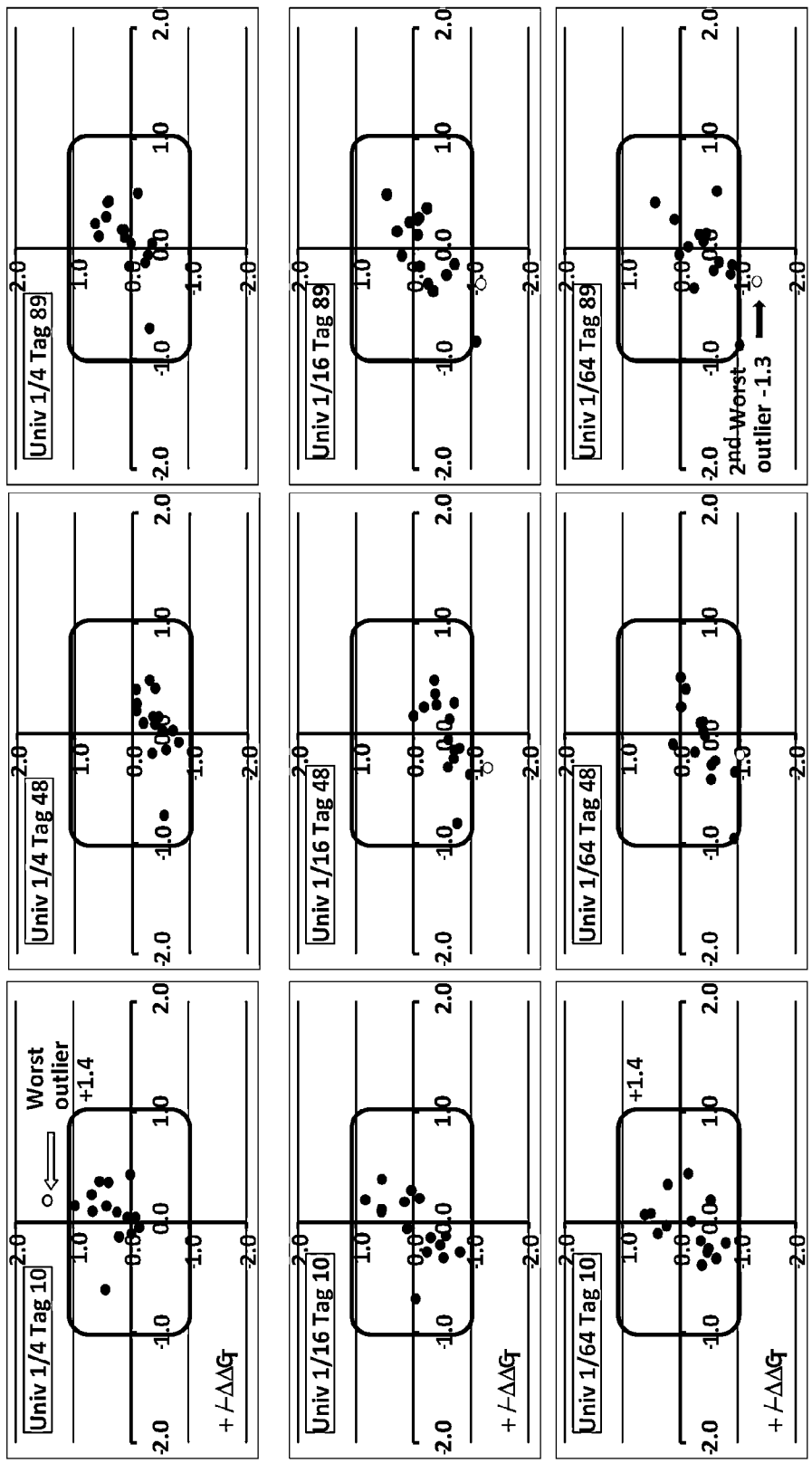
FIG. 7 shows qPCR data derived from 144 serially diluted universal reference cDNA amplified with 3 different tags (Tags 10, 48, and 89) targeting 16 different genes (Example 3). Data are from a single 96.96 array. Since all cDNA samples were dilutions of the same sample, the expected ΔΔCT is 0.96.5% of assays display a ΔΔCT within the highlighted target zone of −1 to +1 cycle. 5-of-144 samples (~3.5%) have a ΔΔCT of 1.0 to 1.4. The two highest outliers with a ΔΔCT of 1.3 and 1.4 are highlighted by arrows. ΔΔCT was calculated by subtracting the control ΔCT gene (Bax) from test ΔCT for each tag/sample dilution/assay combination using universal reference cDNA.

To increase the sample throughput for qPCR, gene expression profiling using a dynamic array without involving a change to chip design, we developed a new protocol. That protocol, (FIGS. 4, 5, and 6) permits examination of mRNA expression levels for 16 genes, present at different levels. FIG. 7 shows the results of analyzing 16 genes in a dilution series of a Universal Reference sample (BioChain) used to validate the dynamic range and ΔΔ Ct measurements of "More Samples" gene expression protocols. In particular, FIG. 7 displays the data derived using a 96.96 DYNAMIC ARRAY® integrated fluidic circuit. This protocol (FIGS. 4, 5, and 6) involved tagging, combining samples, and qPCR. During the tagging step (FIG. 6), sample was divided into 3 separate groups with 48 tag-specific reactions containing differing dilution series. Three sets of 16 forward primers for amplifying 16 cDNAs were synthesized. Each set bears a different tag sequence appended to the 5' end of the forward primers. Each 16 forward primers with the same 5' Tag were pooled together and mixed with 16 gene specific 3' reverse primers to make a multiplex tagging primer mix, one for each Tag. See FIG. 6.

In the tagging step, the 3 separate groups of 4-fold serial (1-in-4,1-in-16, and 1-in-64 fold) dilution of 16 cDNA samples were amplified in a 10 µl reaction containing: 5 µl of 2× PreAmp Master Mix (P/N 4384769; ABI), 2 µl of 5× (250 nM) multiplex tagging primer mix (one separate Tag per sample group), 3 µl of Universal Reference cDNA (Bio Chain). PCR was performed with an initial 15 min at 95° C., followed by 17 cycles of a 2-step amplification profile of 15 sec at 95° C. for denaturation, 4 min at 60° C. for annealing and extension. Samples were diluted 1-in-2 in water and stored at 4° C. These PCR products were treated with 4 µl of EXOSAP-IT® PCR product clean-up (P/N 7800, USB,). See FIG. 5. The 144 samples were reduced to 48 combined samples. The combined sample contains only 1 member of each tag group 1, 2 and 3.

The combined samples were subjected to the PCR on dynamic array chip. 6.5 µl sample mix was prepared for each cDNA mixture containing. 3.5 uL of 2× TAQMAN® Gene Expression Master mix (ABI), 0.35 µL of 20×GE sample loading reagent (Fluidigm) and 2.45 µL of combined sample, as described above. Assay mixes (5 µL) contained: 2.6 µM of 3' nested reverse primer and 2.6 µM hydrolysis probe, 0.25% of Tween 20 and 2 µM of one of the 3 Tag primers (Tag-1 or 2 or 3). Standard Fluidigm gene expression qPCR was performed on 96.96 DYNAMIC ARRAY® integrated fluidic circuits.

Example 4

Use of tRNA in Amplification of Genomic DNA

Human genomic DNA was preamplified using standard protocols on the GENEAMP® PCR system 9700 (Applied Biosystems, CA) in a 25 µl reaction containing 1× PreAmp master mix (Applied Biosystems, CA), 900 nM primers, about 10 ng of DNA sample, and differing amounts of tRNA (transfer ribonucleic acid, from baker's yeast *S. cerevisiae*, Sigma Chemicals, cat no RS636-1ML). Samples were diluted and analyzed by digital PCR on a 12.765 Digital Array commercially available from Fluidigm Corp. (South San Francisco, Calif.). The thermal cycling protocol followed was similar to that reported in Qin J., Jones R C, Ramakrishnan R. (2008) *Studying copy number variations using a nanofluidic platform Nucleic Acids Research*, Vol. 36, No. 18 e116.

Figure 8:
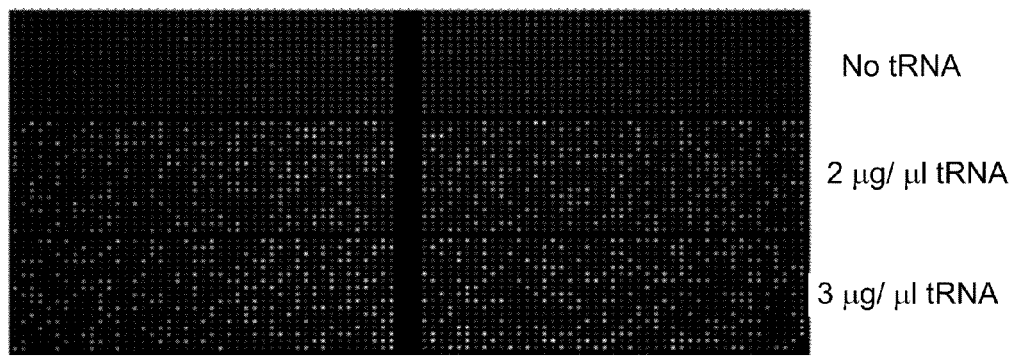
FIG. 8 shows the results of digital PCR on a 12.765 Digital Array commercially available from Fluidigm Corp. (South San Francisco, Calif.). Human genomic DNA was preamplified in the presence of varying amounts of tRNA and then analyzed by digital PCR, as described in Example 4. Specifically, preamplification was performed on human genomic DNA, using protocols described in Qin J., Jones R C, Ramakrishnan R. (2008) *Studying copy number variations using a nanofluidic platform Nucleic Acids Research*, Vol. 36, No. 18 e116 on the GENEAMP® PCR system 9700 (Applied Biosystems, CA) in a 25 µl reaction containing 1× PreAmp master mix (Applied Biosystems, CA), 900 nM primers, ~10 ng of DNA sample and differing amount of tRNA. Samples were diluted and analyzed on the digital array as described in Qin et al. Equal amounts of genomic DNA were used in all panels shown. The upper two panels show the negative controls—preamplification conducted in the absence of tRNA, while the next two pairs of panels show the effects of adding either 2 µg/µl or 3 µg/µl tRNA to the preamplification reaction mix. It is clear that the addition of tRNA increases the intensity of the specific amplification signal and suppresses background.
Figure 9:
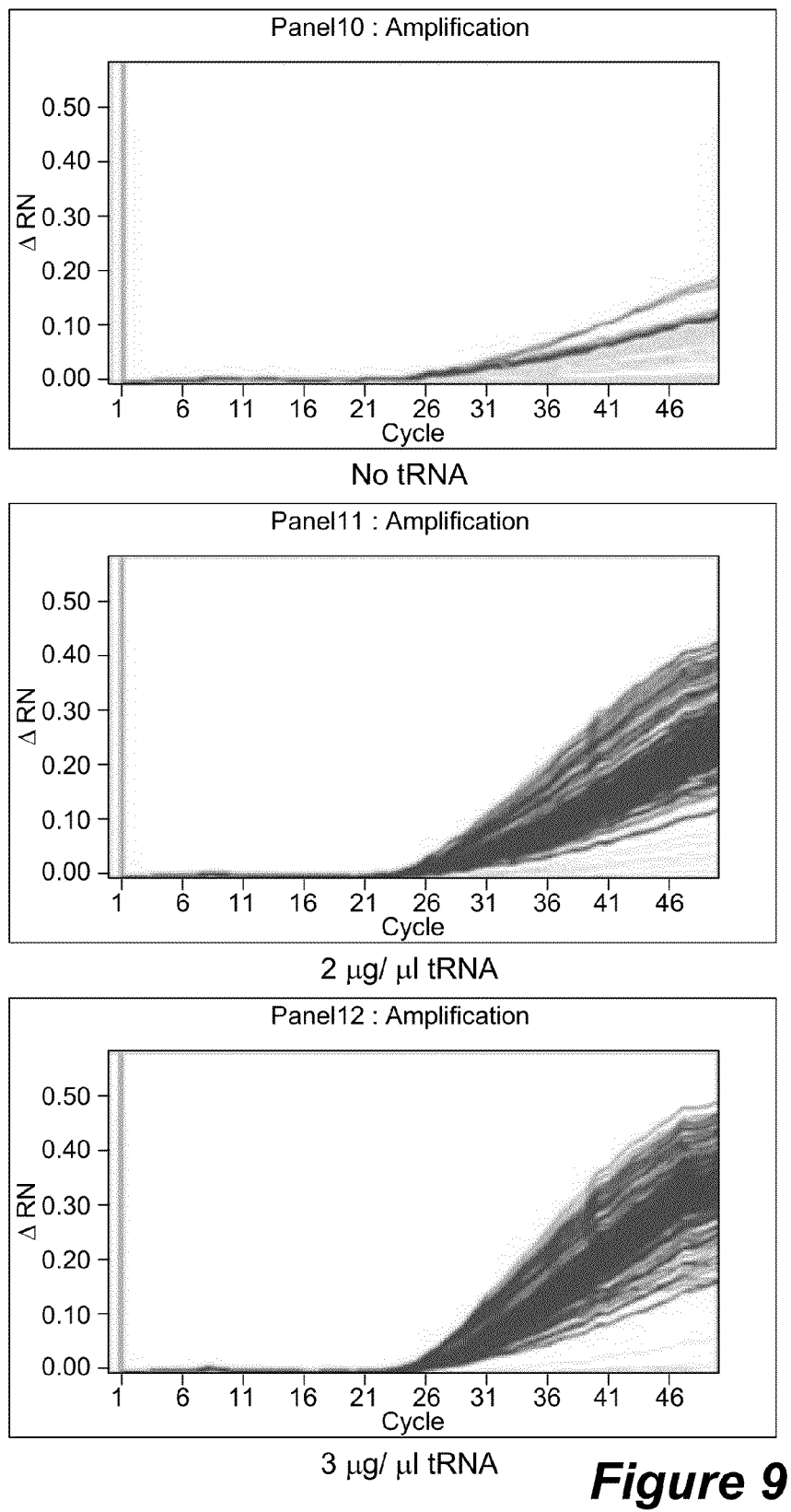
FIG. 9 shows the effect of adding tRNA to preamplification reaction mixtures on the quality of specific amplification curve. The plots shown in FIG. 9 are from the experiment described in Example 4 and reflect real time PCR plots from the same same chip panels shown in FIG. 8. The first panel shows the amplification plot in the absence of tRNA in the preamplification mix, and the second and third panels show the effect when either 2 µg/µl or 3 µg/µl of tRNA was included in the preamplification reaction mix, respectively. The amplification plots confirm the observation from FIG. 8 that the addition of tRNA increases the total amount of specific amplifiable signal, (increase number of hits) and also show that the addition of tRNA improves the quality of amplification (possibly by improving the efficiency of PCR).

FIGS. 8 and 9 demonstrate that the addition of tRNA increases the intensity of the specific amplification signal, suppresses background, and improves the quality of specific amplification curves. Table 2, below, shows the increase in specific counts with the addition of tRNA.

TABLE 2

| Amount of tRNA | Counts* |
|---|---|
| None | 9 |
| 2 µg/µl | 290 |
| 3 µg/µl | 275 |

*Average number of signals per panel of 12.765 Digital Array

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in molecular biology or in the relevant fields are intended to be within the scope of the appended claims.

What is claimed is:

1. An assay method for detecting a plurality of target nucleic acids in a plurality of samples, the method comprising:
   providing S samples that will be mixed together prior to assay, where S is an integer greater than 1;
   separately subjecting each of said S samples to an encoding reaction that produces a set of T tagged target nucleotide sequences, each tagged target nucleotide sequence comprising a sample-specific nucleotide tag and a target nucleotide sequence; wherein T is the number of target nucleic acids to be detected, T being an integer greater than one;
   mixing together tagged target nucleotide sequences from said S samples to form an assay mixture;
   dividing the assay mixture into S×T amplification mixtures, wherein S×T is at least 30, and separately and simultaneously subjecting each of said amplification mixtures to amplification using a unique pair of amplification primers, wherein each amplification primer pair comprises:
      a forward or a reverse amplification primer that anneals to a target nucleotide sequence; and
      a reverse or a forward amplification primer, respectively, that anneals to a sample-specific nucleotide tag; and
   for each unique primer pair, determining whether an amplification product is present in the amplification mixture; and
   if the amplification product is present, determining that a particular target nucleic acid is present in a particular sample; or
   if the amplification product is not present, determining that the particular target nucleic acid is not present in the particular sample.

2. The method of claim 1, wherein:
   said encoding reaction comprises separately subjecting each of said S samples to preamplification using a distinct set of forward and reverse preamplification primers for each sample to produce preamplified samples, wherein
      each preamplification primer set comprises T pairs of forward and reverse preamplification primers, wherein each preamplification primer pair is capable of amplifying a particular target nucleic acid; and
      either all forward preamplification primers or all reverse preamplification primers in a given set comprise a common sample-specific nucleotide tag; and
   said mixing comprises mixing the preamplified samples for each of said S samples to form an assay mixture.

3. The assay method of claim 2, wherein each forward preamplification primer in a set comprises a common sample-specific nucleotide tag, in addition to a target-specific nucleotide sequence, and each reverse preamplification primer in each set comprises a target-specific nucleotide sequence.

4. The assay method of claim 2, wherein each forward preamplification primer in a set comprises a target-specific nucleotide sequence, and each reverse preamplification primer in each set comprises a common sample-specific nucleotide tag, in addition to a target-specific nucleotide sequence.

5. An assay method for detecting a plurality of target nucleic acids in a plurality of samples, the method comprising:
   providing S samples that will be mixed together prior to assay, where S is an integer greater than 1;
   separately subjecting each of said S samples to an encoding reaction that produces a set of T tagged target nucleotide sequences, each tagged target nucleotide sequence comprising a first nucleotide tag linked to a target nucleotide sequence, which is linked to a second nucleotide tag; wherein T is the number of target nucleic acids to be detected, T being an integer greater than one;
   mixing together tagged target nucleotide sequences from said S samples to form an assay mixture;

dividing the assay mixture into S×T amplification mixtures, wherein S×T is at least 30, and separately and simultaneously subjecting each of said amplification mixtures to amplification using a unique pair of amplification primers, wherein each amplification primer pair comprises:
  a forward or a reverse amplification primer that anneals to a first nucleotide tag; and
  a reverse or a forward amplification primer, respectively, that anneals to a second nucleotide tag; and
for each unique primer pair, determining whether an amplification product is present in the amplification mixture; and
if the amplification product is present, determining that a particular target nucleic acid is present in a particular sample; or
if the amplification product is not present, determining that the particular target nucleic acid is not present in the particular sample.

6. The method of claim 5, wherein:
said encoding reaction comprises separately subjecting each of said S samples to preamplification using a distinct set of forward and reverse preamplification primers for each sample to produce preamplified samples, wherein
  each preamplification primer set comprises T pairs of forward and reverse preamplification primers, wherein each preamplification primer pair is capable of amplifying a particular target nucleic acid; and
  each forward preamplification primer comprises a forward nucleotide tag, and each reverse preamplification primer comprises a reverse nucleotide tag; and
said mixing comprises mixing the preamplified samples for each of said S samples to form an assay mixture.

7. The method of claim 5, wherein at least one of said nucleotide tags comprises a sample-specific nucleotide tag that is common to all tagged target nucleotide sequences produced from a given sample.

8. The method of claim 7, wherein the other nucleotide tag is distinct for each tagged target nucleotide sequence in the assay mixture.

9. The assay method of claim 1 or 5, wherein at least one of said amplification primers, comprises at least one nucleotide that is complementary to the target nucleotide adjacent to at least one of said nucleotide tags.

10. The assay method of claim 1 or 5, wherein a series of samples is assayed by preparing a plurality of different assay mixtures, wherein each assay mixture comprises a mixture of S different samples.

11. The assay method of claim 10, wherein S×T is at least a value selected from the group consisting of 48, 96, 120, and 192.

12. The assay method of claim 10, wherein the product of the total number of samples assayed in a single assay ×T is at least a value selected from the group consisting of 2304, 3600, 4608, and 9216.

13. The assay method of claim 2 or 6, wherein amplification mixtures are formed in or, distributed into, separate compartments of a microfluidic device prior to amplification.

14. The assay method of claim 13, wherein the microfluidic device is fabricated, at least in part, from an elastomeric material.

15. The assay method of claim 13, wherein the assay has a dynamic range of at least 4 orders of magnitude.

16. The assay method of claim 2, wherein the preamplification and/or the amplification is carried out by polymerase chain reaction (PCR).

17. The assay method of claim 2 or 6, wherein the preamplification is carried out for 2-20 cycles to introduce the nucleotide tags.

18. The assay method of claim 2 or 6, wherein the preamplification is carried out for a sufficient number of cycles to normalize amplicon copy number across targets and across samples.

19. The assay method of claim 2, wherein the presence of an amplification product is determined by quantitative real-time polymerase chain reaction (qPCR).

20. The assay method of claim 2, wherein a universal qPCR probe is employed in the amplification mixtures to detect amplification products.

21. The assay method of claim 2, wherein one or more target-specific qPCR probes is employed in the amplification mixtures to detect amplification products.

22. The assay method of claim 2 or 6, wherein one or more tag-specific qPCR probes is employed in the amplification mixtures to detect amplification products.

23. The assay method of claim 2, wherein the presence of an amplification product is detected using a fluorogenic nuclease assay.

24. The assay method of claim 23, wherein the presence of an amplification product is detected using a dual-labeled fluorogenic oligonucleotide probe.

25. The assay method of claim 2, additionally comprising quantifying the amount of amplification product in the amplification mixtures.

26. The assay method of claim 25, additionally comprising determining the amount of each target nucleic acid present in each sample.

27. The assay method of claim 2, wherein the assay is performed to determine the copy numbers of the target nucleic acids.

28. The assay method of claim 2, wherein the assay is performed to determine genotypes at loci corresponding to the target nucleic acids.

29. The assay method of claim 2, wherein the assay is performed to determine the expression levels of the target nucleic acids.

30. The assay method of claim 2, additionally comprising, reducing the concentration of preamplification primers prior to carrying out said amplification.

31. The method of claim 2 or 6, wherein the sample comprises a genomic DNA sample.

32. The method of claim 31, wherein the preamplification is conducted in the presence of an amount of a blocking agent that is sufficient to increase specific amplification of the target nucleic acid.

33. The method of claim 32, wherein the blocking agent comprises a nucleic acid blocking agent that hybridizes to repetitive sequences in the genomic DNA sample.

34. The method of claim 32, wherein the blocking agent is selected from the group consisting of tRNA, degenerate oligonucleotide primers, repetitive DNA, bovine serum albumin (BSA), and glycogen.

35. The method of claim 32, wherein the blocking agent is present at a concentration in the range of about 0.1 µg/µl to about 40 µg/µl.

36. The method of claim 35, wherein the blocking agent comprises tRNA at a concentration in the range of about 1 µg/µl to about 5 µg/µl.

* * * * *

SEQUENCE LISTING

<160> NUMBER OF SEQ ID NOS: 3

<210> SEQ ID NO 1
<211> LENGTH: 24
<212> TYPE: DNA

-continued

```
<213> ORGANISM: Artificial Sequence
<220> FEATURE:
<223> OTHER INFORMATION: Nucleotide Tag

<400> SEQUENCE: 1
gtacggtagc agagacttgg tctg                                          24

<210> SEQ ID NO 2
<211> LENGTH: 24
<212> TYPE: DNA
<213> ORGANISM: Artificial Sequence
<220> FEATURE:
<223> OTHER INFORMATION: Nucleotide Tag

<400> SEQUENCE: 2
gacttaatgc tgcttgagac ttgc                                          24

<210> SEQ ID NO 3
<211> LENGTH: 24
<212> TYPE: DNA
<213> ORGANISM: Artificial Sequence
<220> FEATURE:
<223> OTHER INFORMATION: Nucleotide Tag

<400> SEQUENCE: 3
gacatcgtac ctgactcatc gcac                                          24
```